(12) United States Patent
Joshi et al.

(10) Patent No.: US 8,084,753 B2
(45) Date of Patent: Dec. 27, 2011

(54) METHOD AND SYSTEM FOR NON-CONTACT FLUORESCENCE OPTICAL TOMOGRAPHY WITH PATTERNED ILLUMINATION

(75) Inventors: Amit Joshi, Houston, TX (US); Eva Sevick-Muraca, Montgomery, TX (US)

(73) Assignee: Baylor College of Medicine, Houston, TX (US)

( * ) Notice: Subject to any disclaimer, the term of this patent is extended or adjusted under 35 U.S.C. 154(b) by 1292 days.

(21) Appl. No.: 11/688,732

(22) Filed: Mar. 20, 2007

(65) Prior Publication Data

US 2007/0286468 A1 Dec. 13, 2007

Related U.S. Application Data

(60) Provisional application No. 60/743,577, filed on Mar. 20, 2006.

(51) Int. Cl.
*G01N 21/64* (2006.01)
(52) U.S. Cl. .................... 250/459.1; 250/458.1
(58) Field of Classification Search ............... 250/458.1, 250/459.1
See application file for complete search history.

(56) References Cited

U.S. PATENT DOCUMENTS

2004/0015062 A1 * 1/2004 Ntziachristos et al. ....... 600/312
* cited by examiner

*Primary Examiner* — Mark R Gaworecki
(74) *Attorney, Agent, or Firm* — Conley Rose, P.C.

(57) ABSTRACT

A method and system for non-contact fluorescent optical tomography using patterned illumination is disclosed. The method comprises illuminating a surface of a medium with light from at least one excitation light source to project at least two patterns. Each pattern comprises at least one motif, wherein the medium comprises at least one fluorescent target. The method further comprises for each pattern, measuring excitation light reflected from the medium to generate an excitation data set. In addition, the method comprises, for each pattern, measuring fluorescence emitted from the at least one fluorescent target to generate a fluorescence data set. The method also comprises generating a 3D image of the at least one fluorescent target in the medium by applying iterative algorithm. The iterative algorithm minimizes the difference between a predicted data set based on a mathematical model, and each excitation data set and each fluorescence data set.

40 Claims, 25 Drawing Sheets

|  $M_1$ $M_2$ $M_i$ $M_m$ | | $P_1^T$ $P_2^T$ $P_i^T$ $P_m^T$ |
|---|---|---|
| | $R$ | $C_1^T$ $C_2^T$ $C_i^T$ $C_m^T$ |
| $P_1$ $P_2$ $P_i$ $P_m$ | $C_1$ $C_2$ $C_i$ $C_m$ | |

METHOD AND SYSTEM FOR NON-CONTACT FLUORESCENCE OPTICAL TOMOGRAPHY WITH PATTERNED ILLUMINATION

CROSS-REFERENCE TO RELATED APPLICATIONS

This application claims priority to U.S. provisional application Ser. No. 60/743,577, filed on Mar. 20, 2006 and incorporated herein by reference in its entirety for all purposes.

BACKGROUND

1. Field of the Invention

This invention relates generally to the field of molecular imaging. More specifically, the invention relates to fluorescence optical tomography using patterned illumination.

2. Background of the Invention

Molecular imaging is a rapidly advancing research area with the potential of providing early diagnosis and identification of the human diseases. Optical fluorescence tomography is a novel molecular imaging modality that attempts to recover the spatial distribution of light emitting fluorophores inside a highly scattering medium, such as biological tissue, from measurements made on the surface of the medium. This technique offers many advantages including non-invasiveness and the ability to construct 3D images from 2D measurements. The quantification of a non-uniform quantum yield distribution or fluorophore absorption is of major interest in molecular imaging of biological tissue, especially for cancer applications.

Fluorescence optical tomography is typically performed in a model-based framework, wherein a photon transport model is used to generate predicted surface fluorescence measurements for a given fluorescence absorption map in the interior of a medium. More specifically, the interior image is reconstructed by solving an optimization problem by minimizing the difference between observed surface measurements and surface measurements predicted from a physical model. Because photon propagation in a biological medium is diffuse, the image reconstruction problem can be ill-posed. In other words, very different fluorophore distributions can cause similar surface fluorescence measurement profiles. Thus, the quality and information content of the surface fluorescent measurements is crucial to the recovery of a true and accurate interior image.

Prior research has focused on using multiple fiber optics for delivering excitation light and taking fluorescence measurements at different locations on the tissue boundary. However, fiber optics based tomography systems suffer from sparse measurement data, and inadequate excitation light penetration into the tissue interior. This is because only a finite number of optical fibers can be employed without increasing the data acquisition time. In an attempt to solve this problem, area illumination and detection has been investigated. While area-illumination provides enhanced excitation light penetration, the tomography analysis is complex because of the increased ill-posedness introduced by the availability of only the reflectance measurements.

Consequently, there is a need for a method and system of fluorescence optical tomography which can generate dense data sets and enhanced excitation light penetration. Additional needs include reasonable data acquisition time and computationally efficient solutions to the image reconstruction problem.

BRIEF SUMMARY

The methods and systems that will be described provide novel tools for obtaining 3D images of multiple embedded fluorescent targets more efficiently than prior techniques. The invention is simple and does not add significantly more cost to existing methods or systems. Additionally, these methods and systems may be able to resolve fluorescent targets at varying depths more accurately than was previously thought possible.

In an embodiment, a method of imaging comprises illuminating a surface of a medium with light from at least one excitation light source to project at least two patterns. Each pattern comprises at least one motif and the medium comprises at least one fluorescent target. The method further comprises measuring excitation light reflected from the medium to generate an excitation data set. Moreover, the method comprises measuring fluorescence emitted from the at least one fluorescent target to generate a fluorescence data set. Additionally the method comprises generating a 3D image of the at least one fluorescent target in the medium by applying an iterative algorithm. The iterative algorithm minimizes the difference between a predicted data set based on a mathematical model, and each excitation data set and each fluorescence data set.

In another embodiment, a system for imaging comprises at least one excitation light source operable to illuminate a surface of a medium with at least two patterns. The pattern comprises at least one motif and the at least one excitation light source comprises a means for projecting each pattern. The system further comprises a sensor capable of measuring fluorescent light emitted from the fluorescent target and excited light reflected from the medium and a computer capable of executing multiple fluorescence tomography calculations in parallel.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of embodiments of the invention, reference will now be made to the accompanying drawings in which:

FIG. 4 illustrates a system matrix block structure for multiple excitation sources. The index i depicts the experiment number and m is the total number of illumination patterns;

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection, or through an indirect electrical connection via other devices and connections.

The term "pattern" or "patterned" means any design of light on a surface comprising one or more motifs.

The term "motif" means a distinctive element or shape in a pattern which may be repeated.

The term "excitation light" is used to describe light originating from an excitation light source or any light used to excite a fluorescent target.

The term "emitted light" is used to describe fluorescent light emitted from a fluorescent target due to excitation from an excitation light source.

DETAILED DESCRIPTION OF EMBODIMENTS

Figure 1:
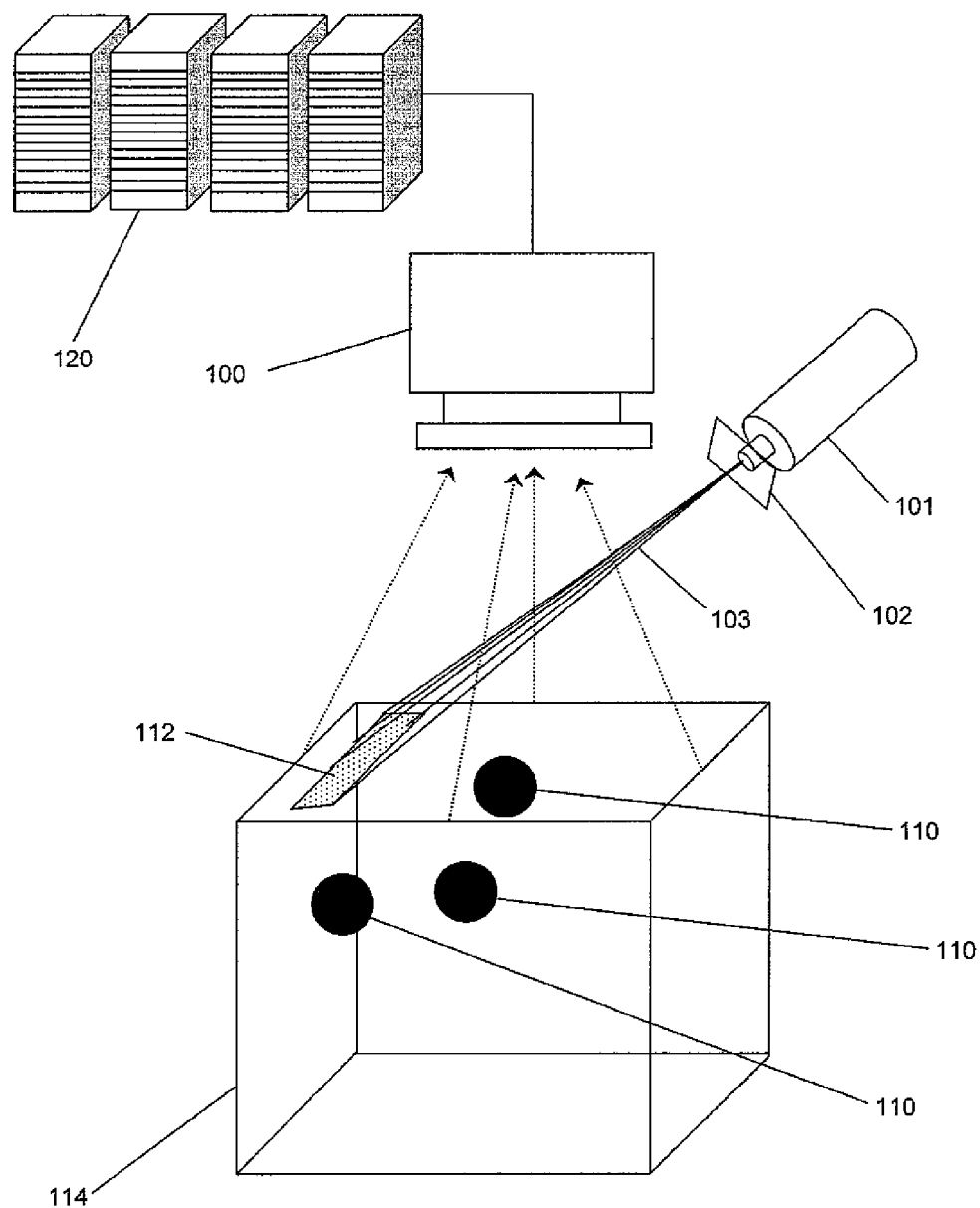
FIG. 1 depicts a schematic of system for fluorescent optical tomography using patterned illumination.

FIG. 1 illustrates a schematic of a system for fluorescent optical tomography using pattern illumination. In an embodiment, at least one excitation light source 101 may illuminate at least two patterns 112 on the surface of a medium 114 in sequence. The excitation light source 101 may comprise any suitable light source. Examples of suitable light sources include without limitation laser diodes, semiconductor laser diodes, gas lasers, or light emitting diodes (LEDs). In an embodiment, the at least one excitation light source 101 comprises a Gaussian light source. As defined herein, a Gaussian light source is a light source in which the spatial distribution of the emitted light is a Gaussian distribution.

In an embodiment, the excitation light source 101 is a time varying light source. Thus, the intensity of the excitation light source 101 may vary with time. In other words, the excitation light source 101 may emit an intensity-modulated light beam. The intensity modulation of excitation light source may comprise without limitation, sinusoidal, square wave, or ramp wave modulation. In addition, the excitation light source 101 may also be pulsed at certain frequencies and repetition rates. The frequency and repetition rates may also be varied with time. The time variation of the excitation light source 101 may be about 1 to about 3 orders of magnitude of the lifetime of the fluorophores used in conjunction with embodiments of the method. Alternatively, the excitation light source 101 is a continuous wave light source which emits a continuous wave light.

In an embodiment, the excitation light source 101 may comprise a means to project at least two patterns 102 on the surface of the medium. The means to project a pattern 102 may manipulate the beam 103 or column of light in any manner such that at least two desired patterns 112 may be projected on the surface, either sequentially or simultaneously. Examples of means for projecting each pattern 102 on to a surface include without limitation, diffractive optics, a beam shaper, or combinations thereof. The means for projecting the patterns 102 may also include a beam splitter to allow for illuminating the medium surface simultaneously with two patterns. In further embodiments, a plurality of excitation light sources 101 may be used. Each light source 101 may be used to simultaneously or sequentially project the same patterns or different patterns on the medium surface. The number of light sources that may be utilized may only be limited by the available computing power and speed needed to perform the tomographic analysis and reconstruct the image.

The medium 114 may comprise fluorescent targets 110. Fluorescent contrast agents may be injected into the medium to enhance image contrast. The medium 114 may comprise tissue, living tissue, a synthetic phantom, a polymer, or combinations thereof. In one embodiment, the medium may comprise the human body or an animal. The fluorescent targets 110 may comprise cancerous cells or tumors tagged with fluorescent agents. In other embodiments, the fluorescent targets 110 may comprise a diseased organ. Furthermore, the fluorescent targets 110 may comprise infectious agents such as without limitation, viruses or bacteria.

Figure 2:
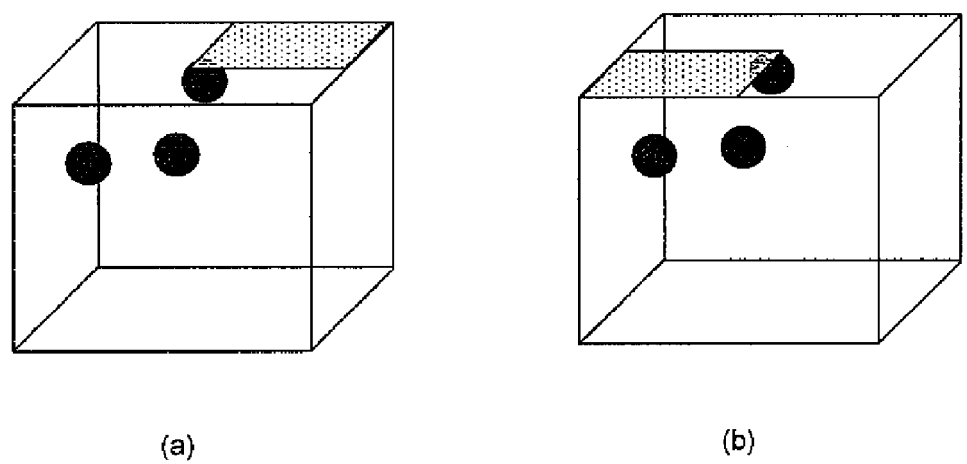
FIG. 2 depicts an example of two different patterns with the same motif.

In certain embodiments, each pattern 112 may comprise a single geometric shape or motif. The motif may be selected from the group consisting of a geometric shape, a polygon, or combinations thereof. Examples of geometric shapes or polygons include without limitation, crosses, ovals, squares, rectangles, triangles, rings, pentagons, octagons, hexagons, or combinations thereof. The motif may comprise at least two edges or boundaries. An edge is a clearly defined line between an illuminated area and an unilluminated area on the surface. For example, a triangle has three edges. A ring has two edges, an inner edge and an outer edge. In other embodiments, an individual pattern may comprise one or more circular motifs such as ovals, dots, circles or combinations thereof. A pattern comprising a single motif may be varied by changing the position of the motif. By way of example only, an illuminated square in the upper right hand quadrant of a larger square is a different pattern than an illuminated square in the lower left hand quadrant of a larger square (See FIGS. 2a & 2b). Thus, the pattern in FIG. 2a is a different pattern than the pattern in FIG. 2b.

In further embodiments, a plurality of motifs may be used. Accordingly, each pattern 112 may comprise any number and/or combination of geometric figures. Each pattern 112 may also comprise a single Gaussian source pattern or a plurality of Gaussian source patterns. As used herein, a Gaussian source pattern is a pattern having a Gaussian spatial distribution. Without being limited by theory, it is believed that utilizing patterns or patterned illumination allows for increased information content for recovering multiple fluorescent targets at varying depths.

In another embodiment, a pattern 112 may be utilized to scan across a medium surface. In such embodiments, the excitation source may further comprise a means for moving the pattern or beam 103. Examples of means for moving the pattern include without limitation, a mirror, a prism, a movable lens, a motor mounted on the excitation source, or combinations thereof. The means for moving the pattern may be controlled by a computer or manually. Alternatively, the excitation source may be manually placed in each desired position for illumination.

In certain embodiments, at least one excitation light source may be used to project a pattern 112 at multiple positions of a medium surface. The number of different positions that may be illuminated may only be limited by the present computing power available. In other embodiments, a plurality of excitation light sources may be used to simultaneously illuminate patterns on multiple positions of a medium surface. Through these novel techniques, denser data sets may be generated by taking multiple fluorescence measurements corresponding to different patterns and different areas of the medium.

The system may also comprise a sensor 100 that is capable of detecting fluorescent light emitted from the fluorescent targets and detecting excitation light reflected from the medium. In an embodiment, the sensor 100 may comprise an intensified charge-coupled camera. Other examples of suitable sensor include without limitation, gated or non-gated EM-CCD cameras. The sensor 100 may further comprise any suitable filters or polarizers necessary to measure the appropriate wavelengths of light required for fluorescent optical tomography.

In a further embodiment, the system may comprise a computer 120 that is capable of executing multiple fluorescent tomographic calculations in parallel. Examples of suitable computers include without limitation, supercomputers, high performance clusters, Linux clusters, parallel processing computers, or workstations. In one embodiment, the computer 120 may comprise a Linux Beowulf cluster with 32 2.2 GHz Opteron 64-bit processors and 4 GB of memory per processor.

Figure 3:
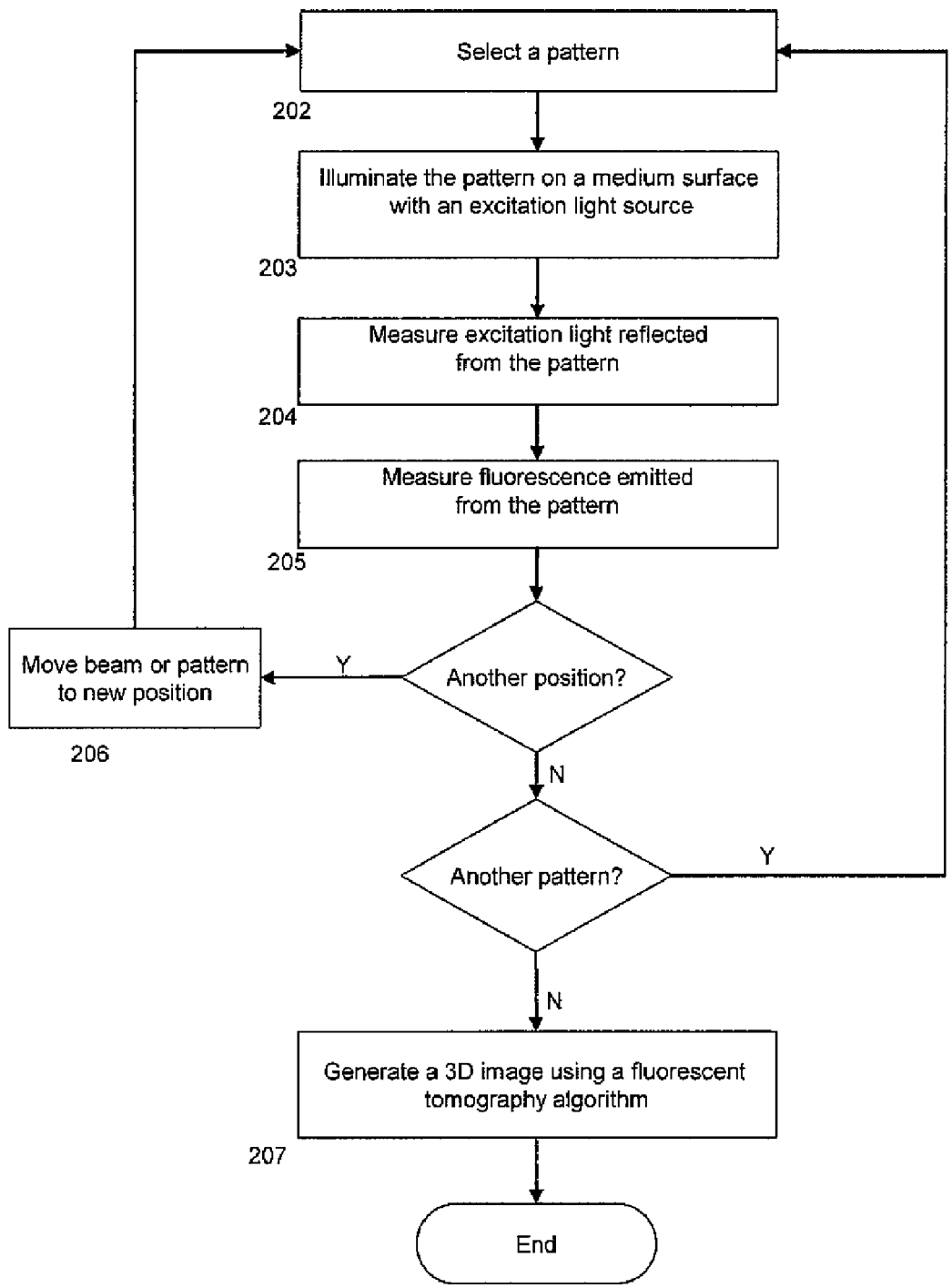
FIG. 3 is a flow chart depicting a method of imaging using fluorescent optical tomography and patterned illumination.

FIG. 3 illustrates a flow diagram of a method 200 for imaging using fluorescent optical tomography with pattern illumination. Method 200 is described with respect to system 100, but method 200 may be implemented with any type of suitable system. Method 200 may begin at step 202 where a suitable pattern may be selected. As discussed earlier, the pattern may comprise any spatially defined variation of light, motif, or shape.

The method 200 further comprises a step 203, wherein the excitation light source illuminates at least two patterns on the surface of a medium. The patterns may be illuminated sequentially or simultaneously. In addition, method 200 may comprise step 204 which may comprise measuring the reflected incident excitation light to generate an excitation data set for each pattern. The incident excitation light is light originating from the excitation source that is reflected from the surface of the medium. Measuring the incident excitation light may comprise the use of one or more polarizers to remove multiply reflected incident excitation light.

The medium may comprise at least one fluorescent target. In other embodiments, the medium may comprise a plurality of fluorescent targets. The light pattern may excite or stimulate the one or more fluorescent targets to emit fluorescent light. In step 205, the emitted fluorescent light may be measured by a sensor as described in system 100 to generate a fluorescence data set. However, the emitted fluorescent light may be measured by any suitable detectors or sensors. Measuring the emitted fluorescence may comprise the use of one or more filters. Examples of suitable filters include without limitation, bandpass filters, holographic filters, tunable filters, etc.

In additional embodiments, steps 202 through 205 may be sequentially repeated for successively different patterns. Measurement data for both emitted light and excitation light may be collected and stored for each pattern or each area of the surface illuminated. In an embodiment, the excitation light source illuminates at least two patterns sequentially. In another embodiment, at least two excitation light sources may be used to simultaneously illuminate different patterns on the medium.

For each pattern, measurement data may be collected and stored. Once the measurement data has been stored, the data may be sent to a computer for analysis in step 207. The number of patterns that may be measured may only be limited by available computing power.

Alternatively, steps 202 to 205 may be repeated as the excitation source illuminates different positions on the surface, i.e., scanning the surface. Thus, the method 200 may further comprise a step 205 where the pattern may be moved to a new position. The excitation beam may be diverted or moved by a means for moving the beam as described earlier. In an embodiment, the same pattern may be used to scan the surface. In other embodiments, a different pattern may be used for each new position. Steps 202 through 205 may be repeated until the entire surface has been scanned. The data measured for each position in steps 204 and 205 may be stored until analyzed in step 207. The number of positions measured may only be limited by the computing power available.

The method 200 may further comprise a step 207, where a 3D image is generated by applying an algorithm to the measured excitation and fluorescence data sets from steps 204 and 205. The algorithm may comprise any suitable algorithm that may be used for fluorescent optical tomography or medical imaging. In an embodiment, the algorithm uses an iterative process to solve a fluorescent tomography problem to reconstruct a 3D image. In a particular embodiment, the algorithm may utilize finite element analysis to generate a 3D image. In further embodiments, the algorithm may comprise an adaptive finite element technique wherein at least one discretization mesh is progressively refined. In other embodiments, the algorithm may comprise a state and parameter discretization mesh, both which are adaptively refined. Generally, the algorithm is an iterative process which minimizes the difference between predicted measurements from a model and the measured experimental data.

In embodiments with multiple measurement data sets, the algorithm may be executed in parallel on a parallel processing computer. As described above, the parallel processing computer may comprise without limitation, a supercomputer, a high performance cluster, a Linux cluster, a workstation, or combinations thereof. Traditional optical tomography schemes utilize only one finite element mesh for the solution of diffusion equations corresponding to different illumination sources realized via fiber optics, while finite element simulations for multiple illumination sources in a non-contact area illumination mode have not been reported in literature till date. Simulation of photon transport via area excitation illumination may utilize careful finite element mesh design to capture the photon fluence variation in the tissue media. For multiple area or pattern illumination sources, optimal meshes can be obtained if the simulations corresponding to different sources are run on separate finite element meshes which are tailored to the illumination source being simulated. This task may be performed efficiently on multiprocessor computers or workstation clusters, wherein each source may be simulated on a separate compute node. The parallelization of Gauss-Newton equations may be aided by the fact that measurements and diffusion equations for different area illumination cases are independent of each other and coupled only by the common set of unknown parameters q. The mathematical aspects of the aforementioned embodiments are described in detail below.

To aid in understanding various mathematical aspects of the method, the following table of selected variables is listed:

| | |
|---|---|
| R | Position |
| x | excitation light field subscript |
| m | emission light field subscript |
| u | complex-valued photon fluence field at excitation wavelength |
| v | complex-valued photon fluence field at emission wavelength |
| D | photon diffusion coefficient |
| $\mu_{ax,mi}$ | absorption coefficient due to endogenous chromophores |
| $\mu_{ax,mf}$ | absorption coefficient due to exogenous fluorophores |
| $\mu'_{sx,m}$ | reduced scattering coefficient |
| $\omega$ | modulation frequency |
| $\phi$ | quantum efficiency of the fluorophore |
| $\tau$ | fluorophore lifetime associated with first order fluorescence decay kinetics |
| M | number of light sources |
| S(r) | excitation boundary source |
| n | outward normal to the surface |
| $\gamma$ | constant depending on the optical reflective mismatch at boundary |
| $\beta$ | Tikhonov regularization parameter |
| $\lambda_i^{ex}$ | Lagrange multiplier corresponding to the excitation diffusion equation |
| $\lambda_i^{em}$ | Lagrange multiplier corresponding to the emission diffusion equation |
| q | The parameter $\mu_{axf}$ |

Generally, step 205 may use finite element techniques to reconstruct a 3D map of the fluorescence absorption coefficients, which are directly proportional to the position of the fluorophores. More specifically, a photon transport model may be used to predict boundary fluorescence measurements for a given fluorescence absorption map in the tissue interior. The absorption map may then be iteratively updated until the predicted boundary fluorescence measurements converge to the actual experimentally observed fluorescence measurements. For photon propagation in large tissue volumes, the following set of coupled photon diffusion equations are an accurate model:

$$-\nabla \cdot [D_x(r)\nabla u(r,\omega)] + k_x u(r,\omega) = 0 \quad (1)$$

$$-\nabla \cdot [D_m(r)\nabla v(r,\omega)] + k_m v(r,\omega) = \beta_{xm} u(r,\omega) \quad (2)$$

Here, $$D_{x,m} = \frac{1}{3(\mu_{ax,mi} + \mu_{ax,mf} + \mu'_{sx,m})}$$

$$k_{s,m} = \frac{i\omega}{c} + \mu_{ax,mi}(r) + \mu_{ax,mf}(r)$$

$$\beta_{xm} = \frac{\phi \mu_{axf}}{1 - i\omega\tau(r)}$$

These equations are complemented by Robin-type boundary conditions on the boundary $\partial\Omega$ of the domain $\Omega$ modeling the NIR excitation source:

$$2D_x \frac{\partial u}{\partial n}\gamma u + S(r) = 0, \; 2D_m \frac{\partial v}{\partial n}\gamma r = 0 \quad (3)$$

The complex-valued function S(r) is the excitation boundary source. There is no source term for the emission boundary condition. The goal of fluorescence tomography is to reconstruct the spatial map of coefficients $\mu_{axf}(r)$ and/or $\tau(r)$ from measurements of the complex emission fluence v on the boundary. $\mu_{axf}(r)$ will be the primary coefficient to be recovered. For notational brevity, $q=\mu_{axf}$ in the following paragraphs.

A novel fluorescence tomography algorithm utilizing adaptive finite element methods has previously been proposed in A. Joshi, W. Bangerth, and E. M. Sevick-Muraca, Optical Express 12, 5402 (2004), which is herein incorporated by reference in its entirety for all purposes. The formulation of the scheme and its application to image reconstructions from multiple area illumination sources may be implemented as follows.

M different area excitation light sources ($S^i(r)$, i=1, 2 ... M) may be employed to excite the embedded fluorophore in the phantom. Fluorescence measurements are taken on the illumination plane. The fluorescence image reconstruction problem is posed as a constrained optimization problem wherein an $L_2$ norm based error functional of the distance between boundary fluorescence measurements $z=\{z_i, i=1, 2 \ldots m\}$ and the diffusion model predictions $v=\{v^i, i=1, 2 \ldots m\}$ is minimized by variation of the parameter q, with the additional constraint that the coupled diffusion model corresponding to each illumination source ($A^i(q, [u^i, v^i])=0$) is satisfied. In a function space setting this minimization problem reads as:

$$\min_{q,u,v} J(q,v) \text{ subject to } A^i(q;[u^i,v^i])([\zeta^i,\xi^i]) = 0, \; i=1,2\ldots M \quad (4)$$

Here, the error functional J(q, v) incorporates a least square error term over the measurement part $\Gamma$ of the boundary $\partial\Omega$ and a Tikhonov regularization term:

$$J(q,v) = \sum_{i=1}^{i=m} \frac{1}{2}\|v^i - z^i\|_r^2 + \beta r(q) \quad (5)$$

The constraint $A^i(q; [u^i, v^i])([^3 i, \gg i])=0$ is the weak or variational form of the coupled photon diffusion equations in frequency domain with partial current boundary conditions for the $i^{th}$ excitation source, and with test functions $[\zeta,\xi]\epsilon H^1(\Omega)$:

$$A^i(q;[u^i,v^i])([\zeta^i,\xi^i]) = \quad (6)$$

$$(D_x\nabla u^i, \nabla \zeta^i)_\Omega + (k_x u^i, \zeta^i)_\Omega + \frac{\gamma}{2}(u^i, \zeta^i)_{\partial\Omega} + \frac{1}{2}(S^i, \zeta^i)_{\partial\Omega} +$$

$$(D_x\nabla v^i, \nabla \xi^i)_\Omega + (k_m v^i, \xi^i)_\Omega + \frac{\gamma}{2}(v^i, \xi^i)_{\partial\Omega} - (\beta_{xm}, u^i, \xi^i)_\Omega$$

The solution of minimization problem (4) is determined as a stationary point of the Lagrangian $$L(x) = J(q, v) + \sum_{i=1}^{i=m} A^i(q;[u^i, v^i])([\lambda_i^{ex}, \lambda_i^{em}]) \quad (7)$$

Here, $\lambda_i^{ex}, \lambda_i^{em}$ are the Lagrange multipliers corresponding to the excitation and emission diffusion equation constraints for the $i^{th}$ source, respectively. The abbreviation $x=\{u, v, \lambda^{ex}, \lambda^{em}, q\}$ is used for simplicity. A stationary point of $L(x)$ is found using the Gauss-Newton method wherein the update direction $\delta u_k = \{\delta u_k, \delta v_k, \delta \lambda_k^{ex}, \delta \lambda_k^{em}, \delta q_k\}$ is determined by solving the linear system $$L_{xx}(x_k)(\delta x_k, y) = -L(x_k, y) \forall y \quad (8)$$

where $L_{xx}(x_k)$ is the Gauss-Newton approximation to the Hessian matrix of second derivatives of L at point $x_k$, and $y$ denotes the possible test functions. These equations represent one condition for each variable in $\partial x_k$. Once the search direction is computed from Eq. (8), the actual update is determined by calculating a safeguarded step length $\alpha_k$:

$$x_{k+1} = x_k + \alpha_k \delta x_k \quad (9)$$

The step-length $\alpha_k$ can be computed from one of several methods, such as the Goldstein-Armijo backtracking line search. The Tikhonov regularization term $\beta r(q)$ added to the minimization functional $J(q, v)$ defined in Eq. (5) is used to control undesirable components in the map $q(r)$ that result from a lack of resolvability. The Gauss-Newton equations are discretized by the finite element method. State and adjoint variables u, v, ex, and, em are discretized and solved for on a mesh with continuous finite elements, while the unknown parameter map q is discretized on a separate mesh with discontinuous finite elements. Whenever Gauss-Newton iterations on these meshes have reduced the error function by a factor of $10^{-3}$ or the Gauss-Newton step length returned by the line search algorithm has fallen below 0.15, both meshes are refined using a posteriori refinement criteria. The discretized Gauss-Newton system has the following components:

$$\begin{bmatrix} M & 0 & P^T \\ 0 & R & C^T \\ P & C & 0 \end{bmatrix} \begin{bmatrix} \delta p_k \\ \delta q_k \\ \delta d_k \end{bmatrix} = \begin{bmatrix} F_1 \\ F_2 \\ F_3 \end{bmatrix} \quad (10)$$

where the updates for the primal and dual(Lagrange) variables are abbreviated as $\delta p_k = [\delta u_k, \delta v_k]^T$, $\delta d_k = [\delta \lambda_k^{ex}, \delta \lambda_k^{em}]^T$. Here, $M = \{M_1, M_2 \ldots M_m\}$ is the measurement error function for all the excitation sources; $P = \{P_1, P_2 \ldots P_m\}$ is the representation of the discrete forward diffusion model for all the excitation illumination sources. The matrix $C = \{C_1, C_2 \ldots C_m\}$ is obtained by differentiating the semi-linear form $A_i$ in Eq. (6) with respect to the parameter q. The detailed formulation of the individual blocks $M_i$, $P_i$, $C_i$ and the right hand side F is provided in reference [3] for the single excitation source experiments. The block structure of the Gauss-Newton KKT matrix (10) is depicted in FIG. 4. The Schur complement solution of the KKT system (10) is written as $$\left\{ R + \sum_{i=1}^{i=m} C_i^T P_i^{-T} M_i P_i^{-1} C_i \right\} \delta q_k = F_2 - \sum_{i=1}^{i=m} C_i^T P_i^{-T} (F_1 - M_i P_i^{-1} F_3), \quad (11)$$

$$P_i \delta p_k^i = F_3 - \sum_{i=1}^{i=m} C_i \delta q_k^i, \quad (12)$$

$$P_i^{-T} \delta d_k^i = F_3 - \sum_{i=1}^{i=m} M_i \delta p_k^i \quad (13)$$

The individual forward solutions $P_i^{-1}$ may be implemented on separate computers or separate processors on a multiprocessor system. On a workstation cluster with m nodes, the image reconstruction task may be performed at approximately the same cost as for a single excitation source. Equations (11)-(13) are iteratively solved till convergence to obtain the unknown fluorescence map q. Further implementation details involving the line search procedure and the incorporation of bounds on the unknown parameters are identical to the single excitation source based image reconstruction as described in Joshi et. al. The computations are implemented in an object oriented C++ based programming framework developed in W. Bangerth (PhD Dissertation, University of Heidelberg, 2002), which is hereby incorporated by reference in its entirety for all purposes.

To further illustrate various illustrative embodiments, the following examples are provided.

EXAMPLE 1

Figure 5:
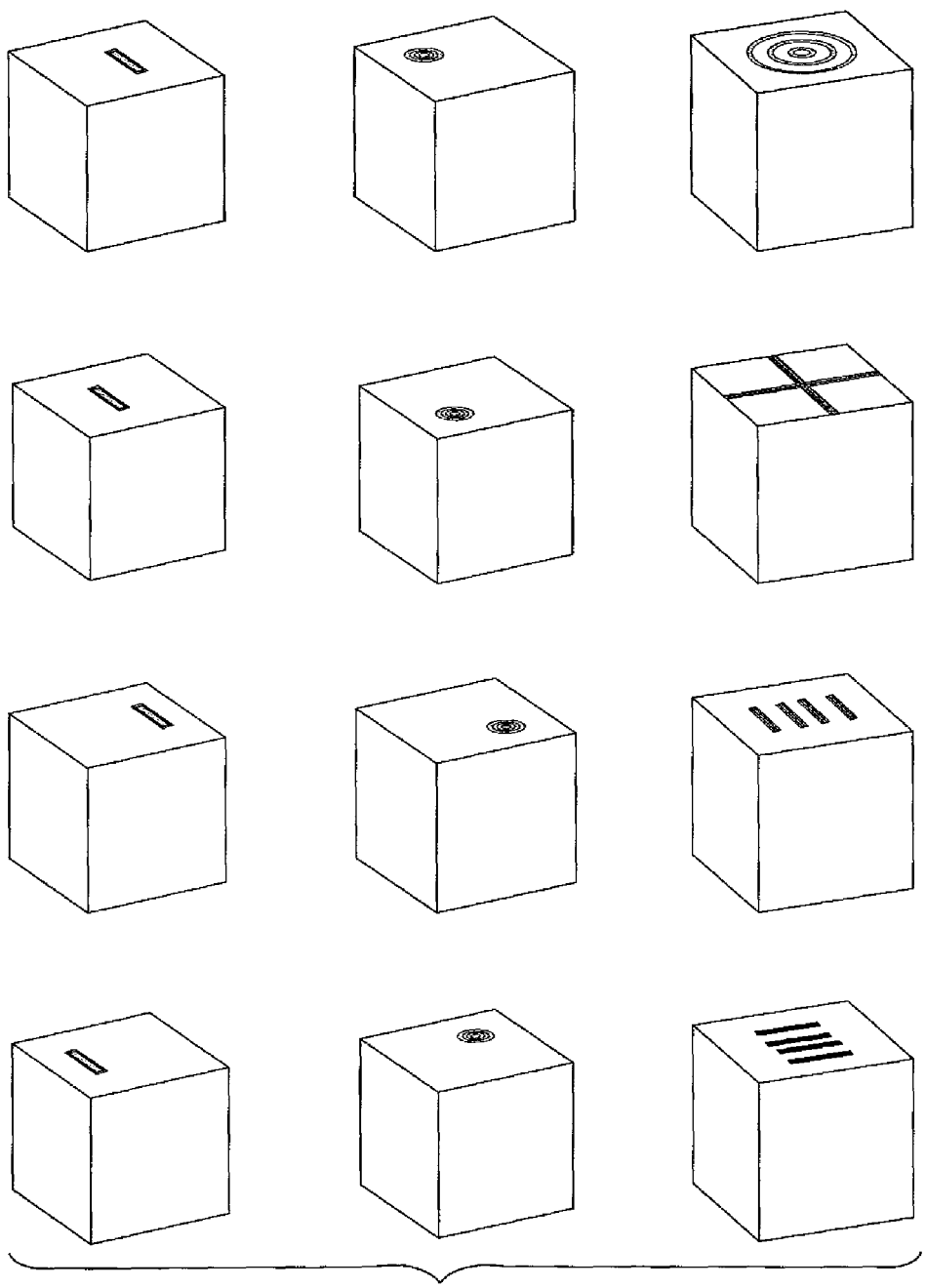
FIG. 5 illustrates examples of patterns that may be used in multiple source fluorescence optical tomography.

Synthetic measurements were generated on a 512 ml cubical tissue phantom with optical properties of 1% Liposyn. In a right handed coordinate system with the origin at the vertex of the phantom, z=8 plane was set as the illumination and detection plane. Excitation light modulated at 100 MHz was delivered on the illumination plane via a multiple illumination scheme employing (i) four line sources, (ii) four Gaussian sources, and (iii) a combination of diffractive optics patterns. These source patterns are depicted in FIG. 5. The simulated fluorescence amplitude and phase was collected over the illumination plane. On a workstation cluster, the maximum number of sources which can be simulated is only limited by the number of compute nodes. The fluorescent targets were simulated to be 5 mm diameter spheres filled with 1 µM Indocyanine Green solution in 1% liposyn. The phantom background was assumed to be devoid of fluorophores.

A. Single Target Reconstruction

Figure 6A:
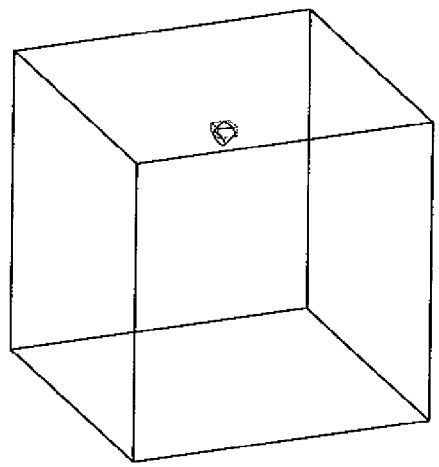
FIG. 6 illustrates single target reconstructions for: scanning lines (left), scanning Gaussians (center), and diffractive optics patterns (right)
Figure 6B:
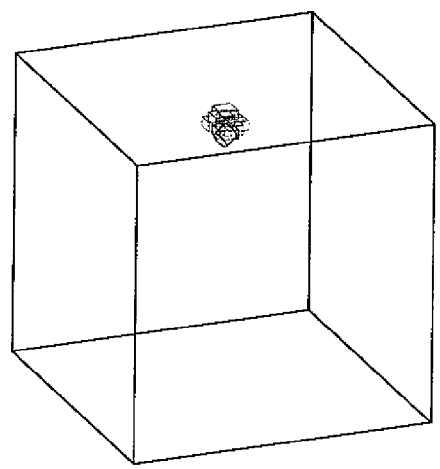
Figure 6C:
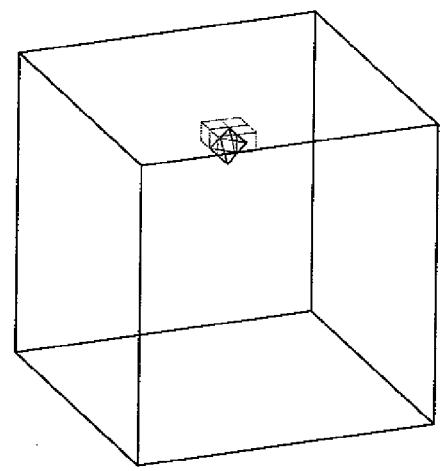
Figure 7A:
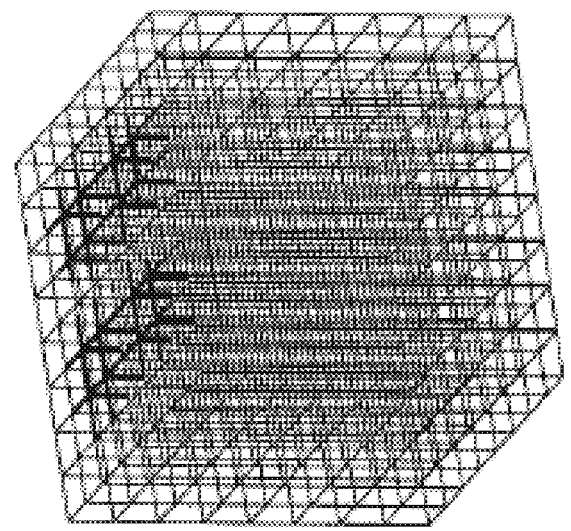
FIGS. 7A-E illustrate 5 automatic state mesh refinements for the following single source patterns, represented are: line (left), Gaussian source (center), and diffractive (right) optics pattern.
Figure 7A:
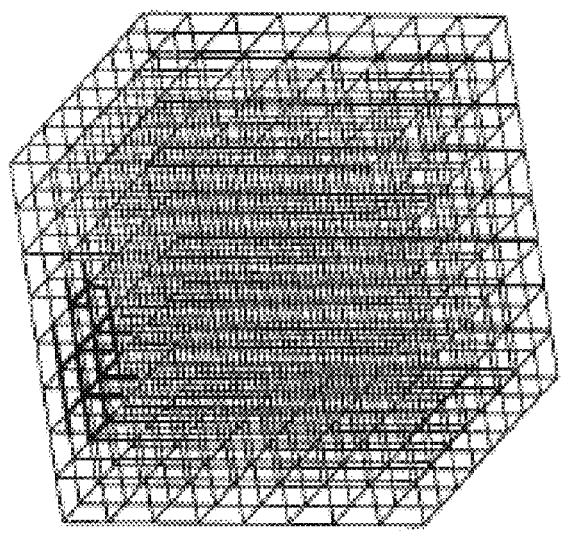
Figure 7A:
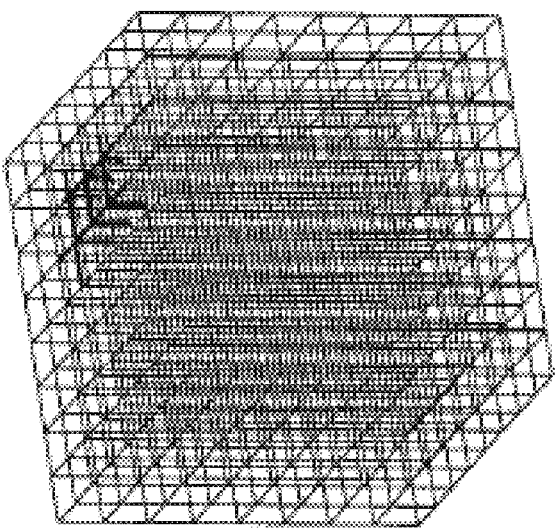
Figure 7B:
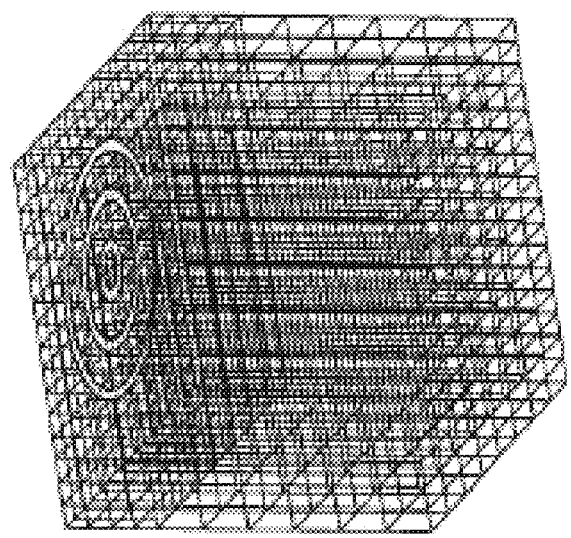
Figure 7B:
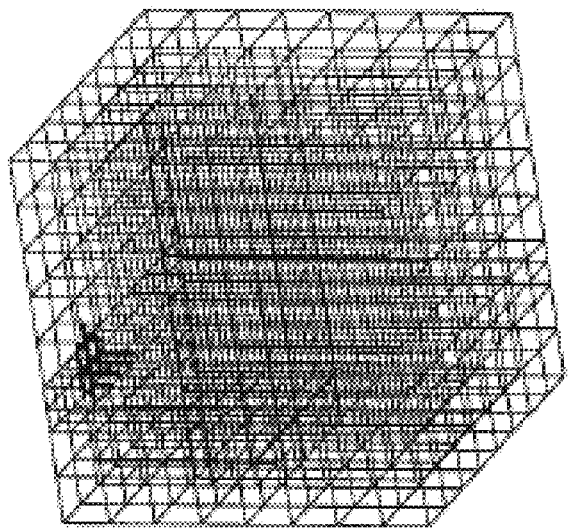
Figure 7B:
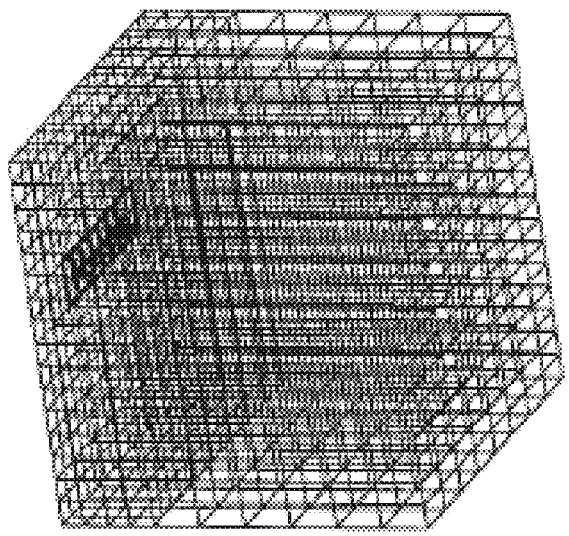
Figure 7C:
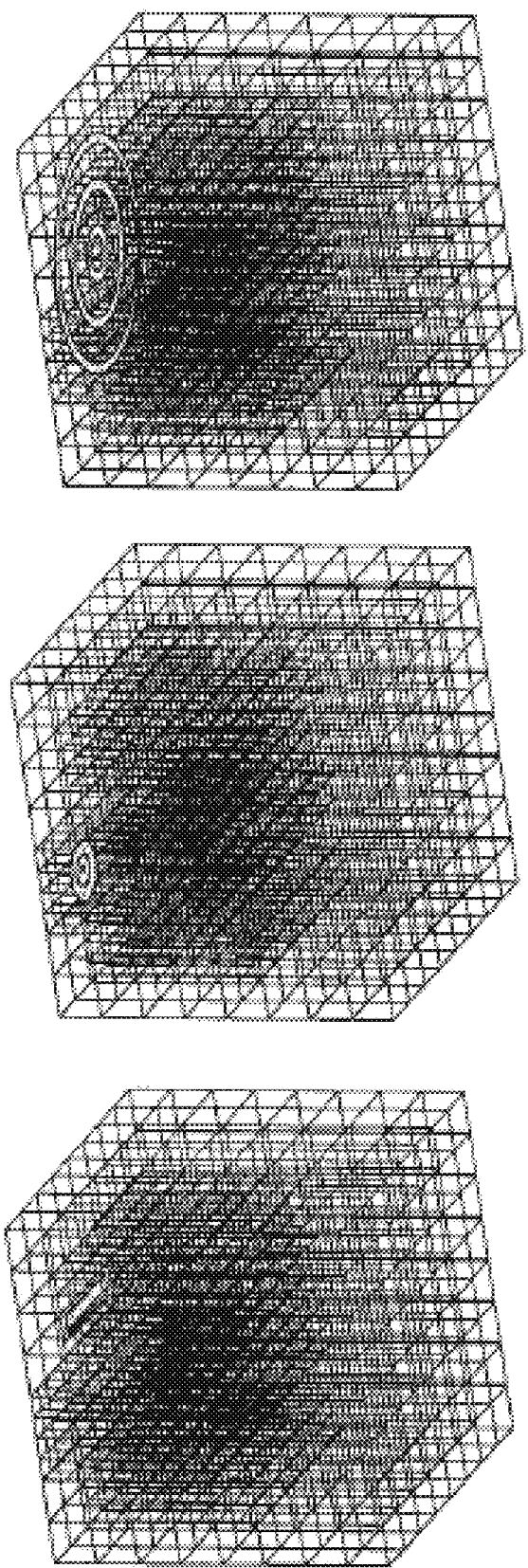
Figure 7D:
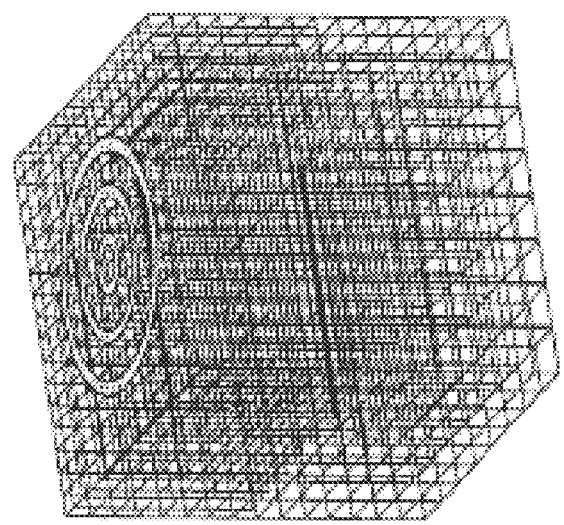
Figure 7D:
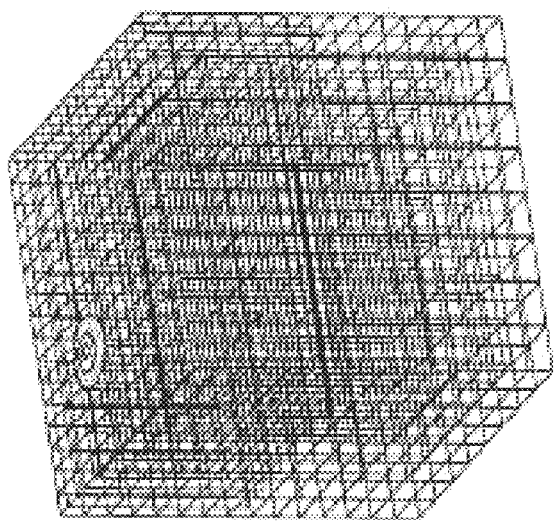
Figure 7D:
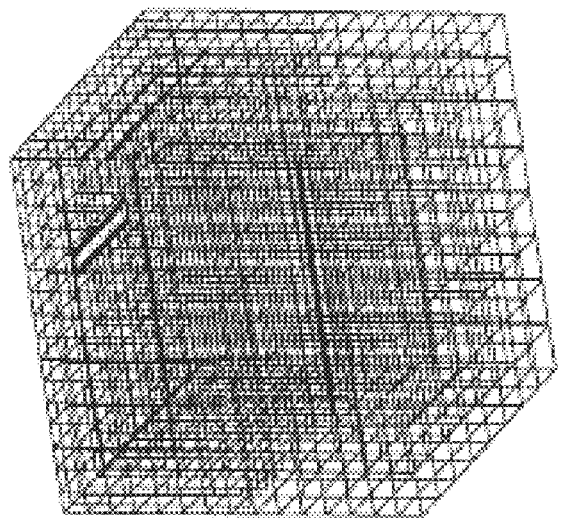
Figure 7E:
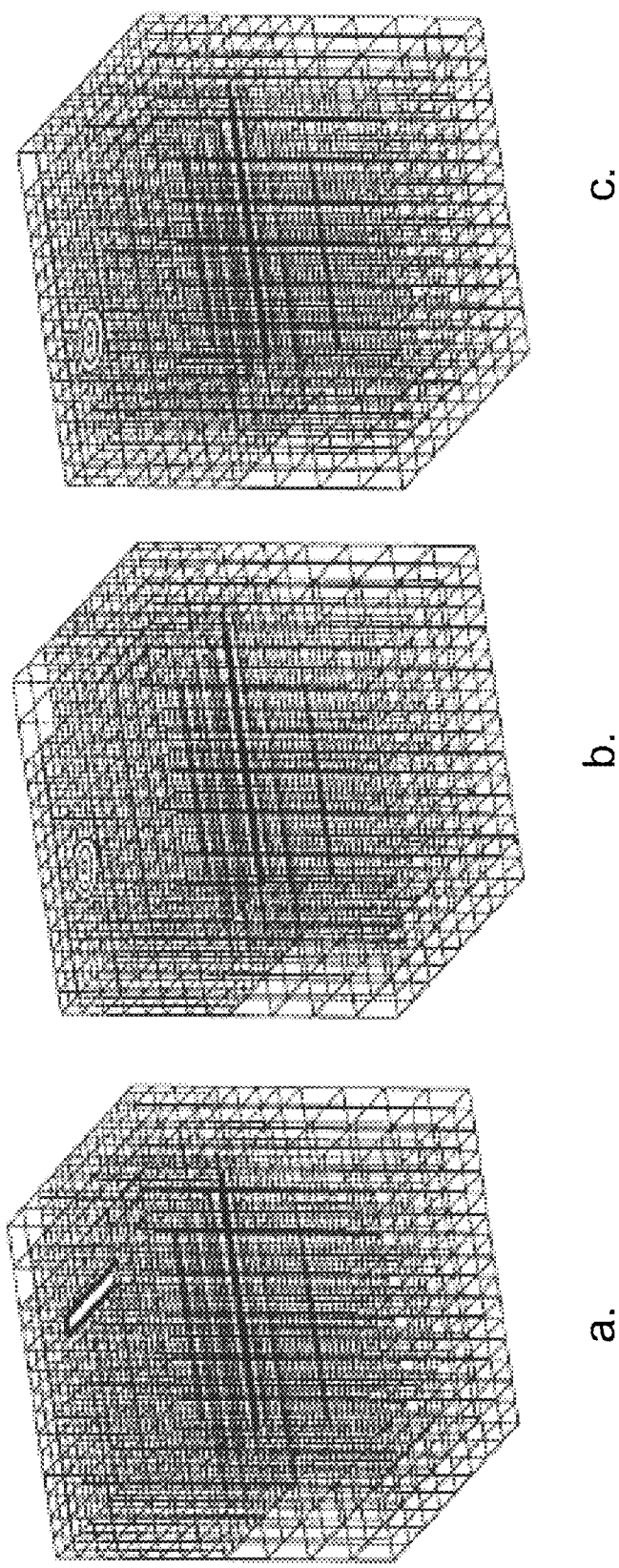
Figure 8A:
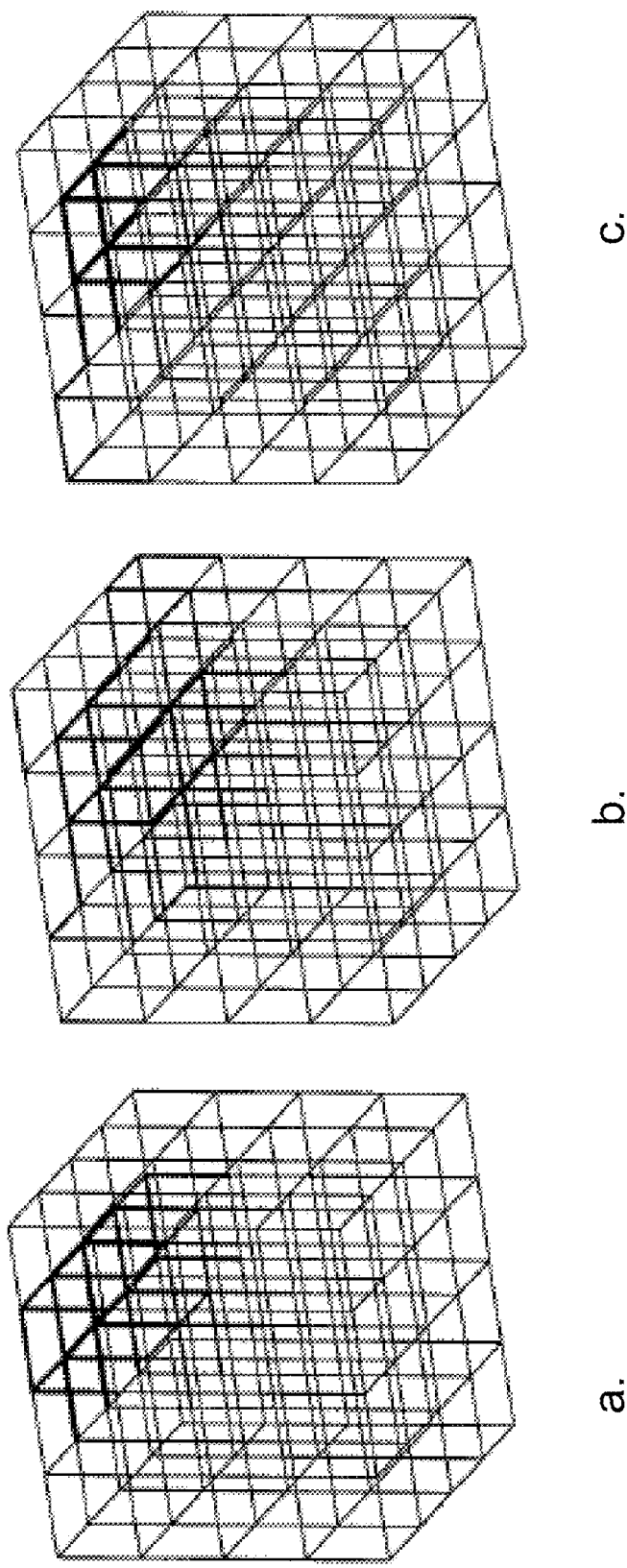
FIGS. 8A-E illustrate 5 automatic parameter mesh refinements for the following single source patterns, represented are: line (left), Gaussian source (center), and diffractive (right) optics pattern.
Figure 8B:
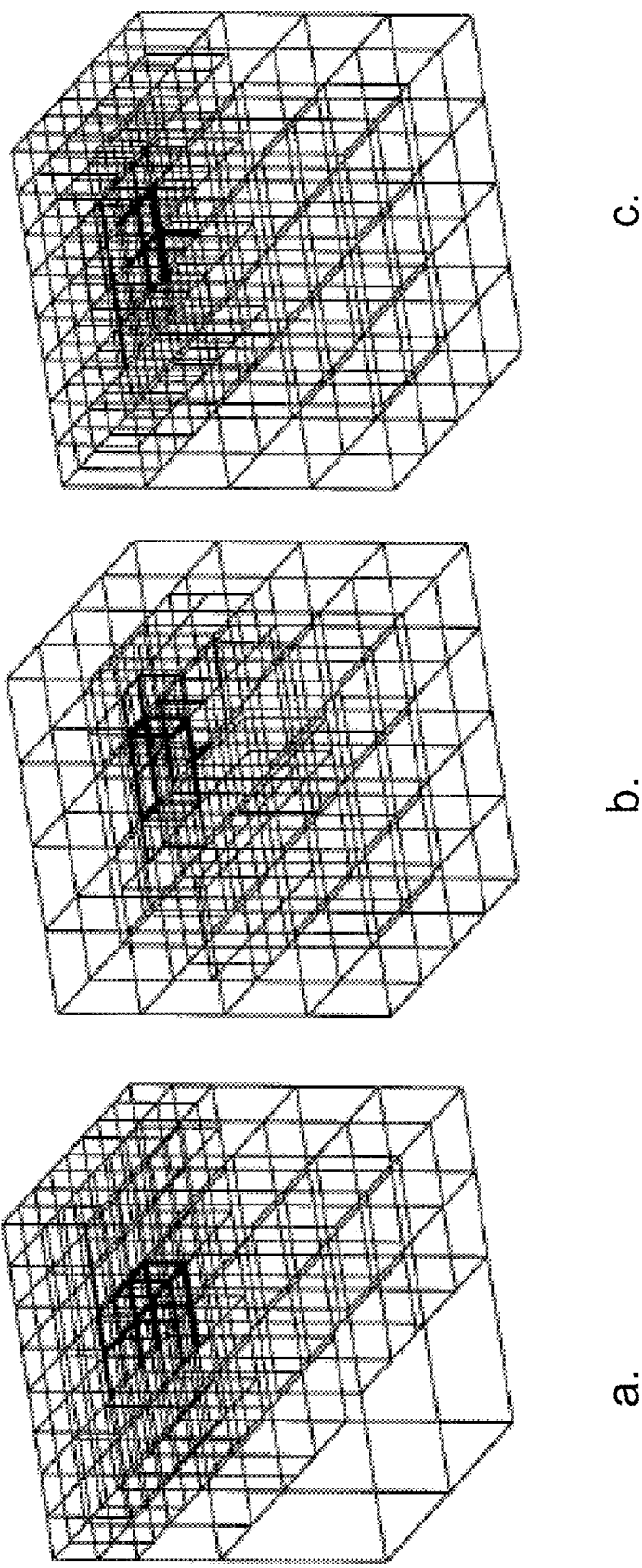
Figure 8C:
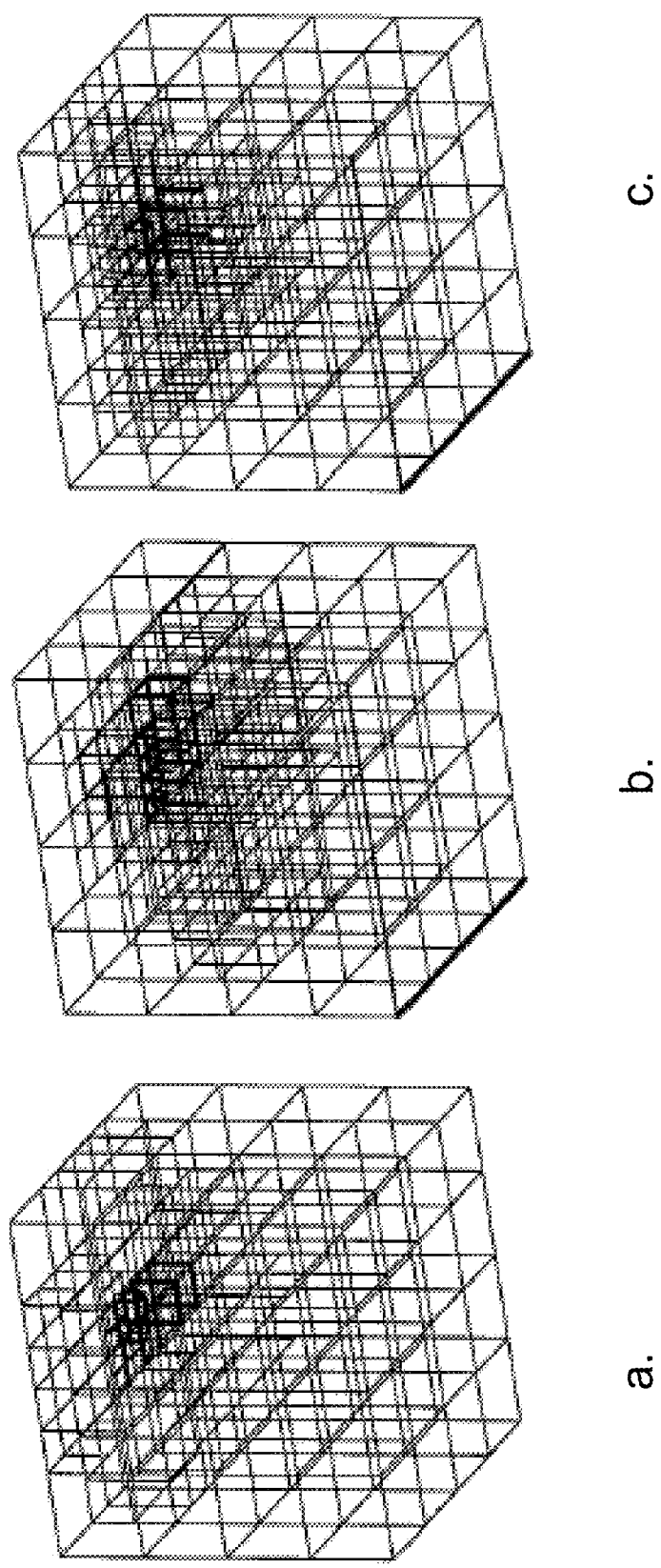
Figure 8D:
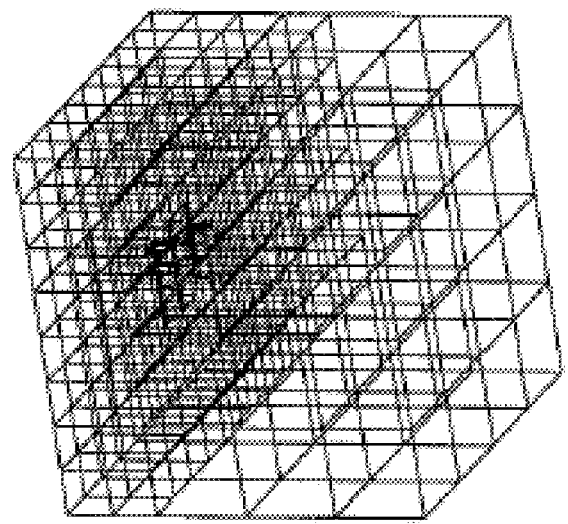
Figure 8D:
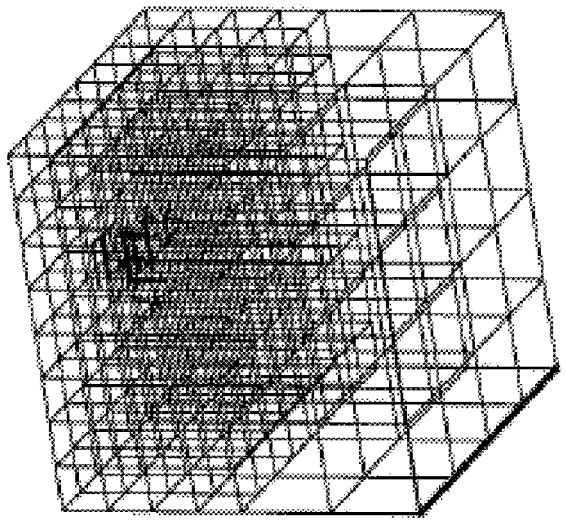
Figure 8D:
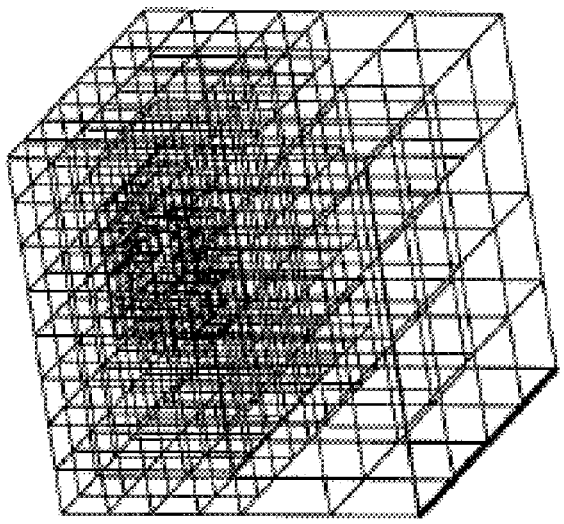
Figure 8E:
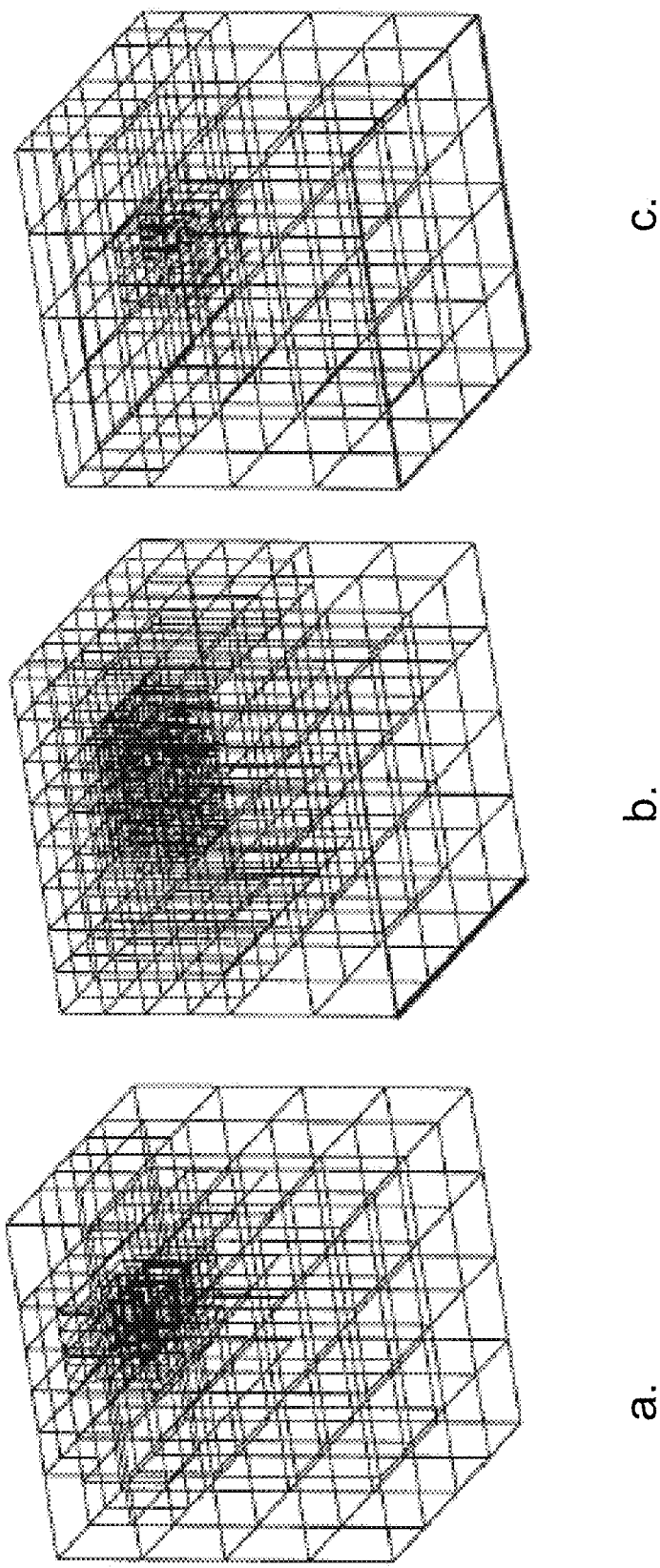
Figure 9A:
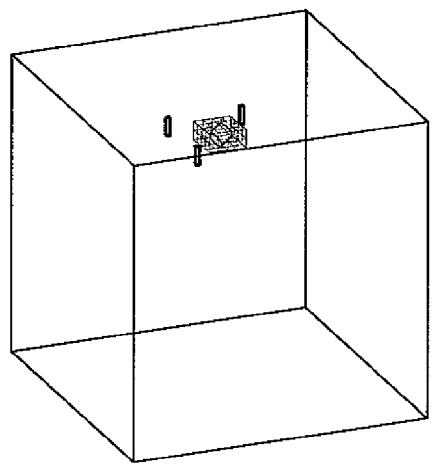
FIG. 9 illustrates three-target reconstructions for: a) a single Gaussian source, b) multiple line sources, c) multiple Gaussian sources, d) multiple diffractive optics patterns.
Figure 9B:
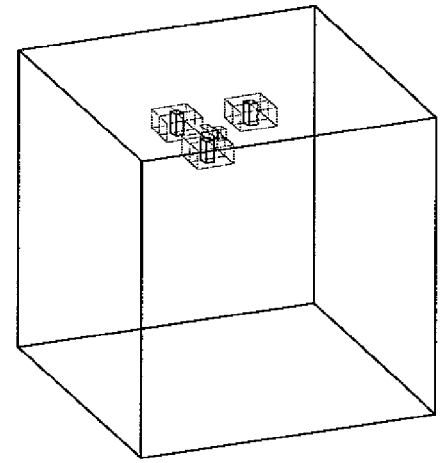
Figure 9C:
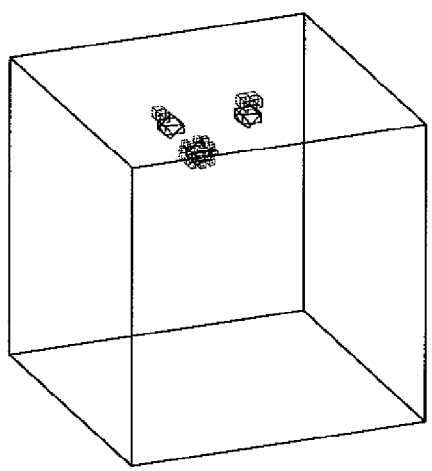
Figure 9D:
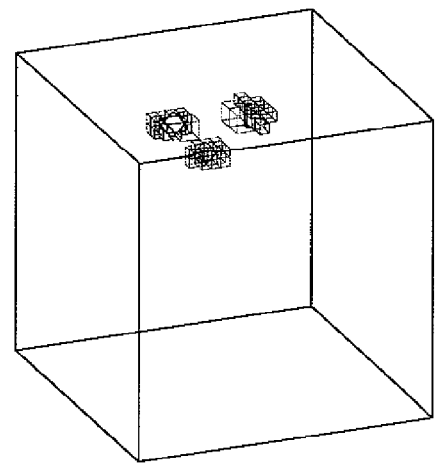

The simulated fluorescent target was placed at the depth of 1 cm from the illumination plane, synthetic fluorescence measurement data was generated by the adaptive finite element solution of coupled diffusion equations for multiple source patterns and image reconstruction performed by the procedure explained. FIG. 6 depicts the reconstructed images obtained for source patterns (i) to (iii). All three incident source illumination patterns are able to recover the embedded fluorescent target. However the recovered target for the multiple Gaussian source patterns shifted towards the illumination plane, which made sense as the target location was farthest from the excitation sources in this case, and hence, less excitation light reached the fluorophore, resulting in lower signal for image reconstruction.

If a top 10% cutoff is established for the recovery of the contours of the fluorescent target, then the recovered target size varies with the type of incident illumination patterns used. Diffractive optics patterns illuminate the largest portion of the illumination plane and result in a reconstructed image with the maximum lateral spread. FIGS. A-E depict the evolution of state (forward solution) mesh with the progress of Gauss-Newton iterations for all three excitation patterns. To convey the essential idea, only the mesh corresponding to the first source is depicted. It is clear that for resolving complex source patterns generated by diffractive optics, adaptive mesh refinement is a necessity as during the first couple of refinement stages, the incident excitation source is poorly resolved and at least 4 adaptive refinements are required. Resorting to a priori global mesh refinement will require exorbitant computational burden in the simulation of scanning and patterned area incident illumination.

FIGS. 8A-E illustrate the parameter mesh evolution. The mesh is refined near the boundary of the reconstructed fluorescent target and coarsened elsewhere.

B. Multiple Target Reconstructions

Figure 10A:
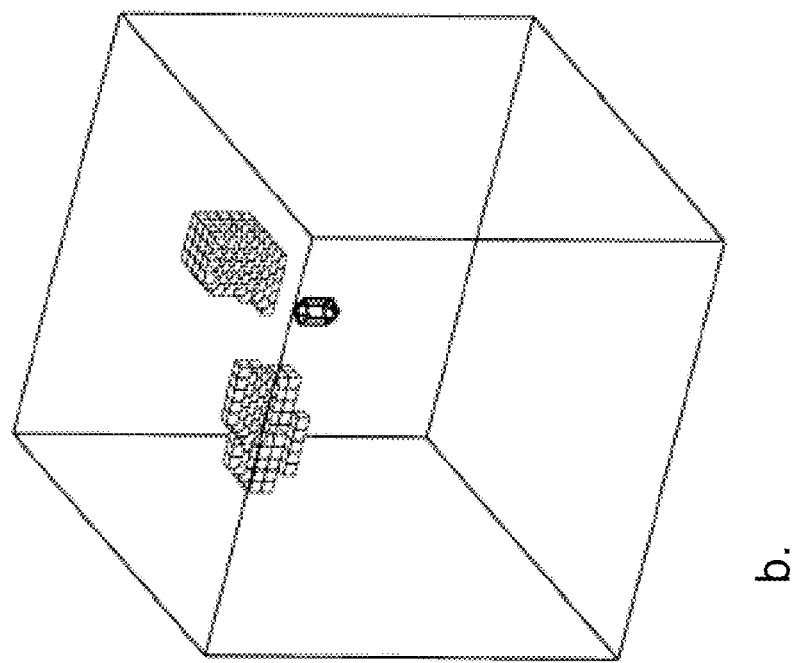
FIGS. 10A-C illustrate varying depth three-target reconstructions for: a) a single Gaussian source, b) multiple line sources, c) multiple Gaussian sources.
Figure 10A:
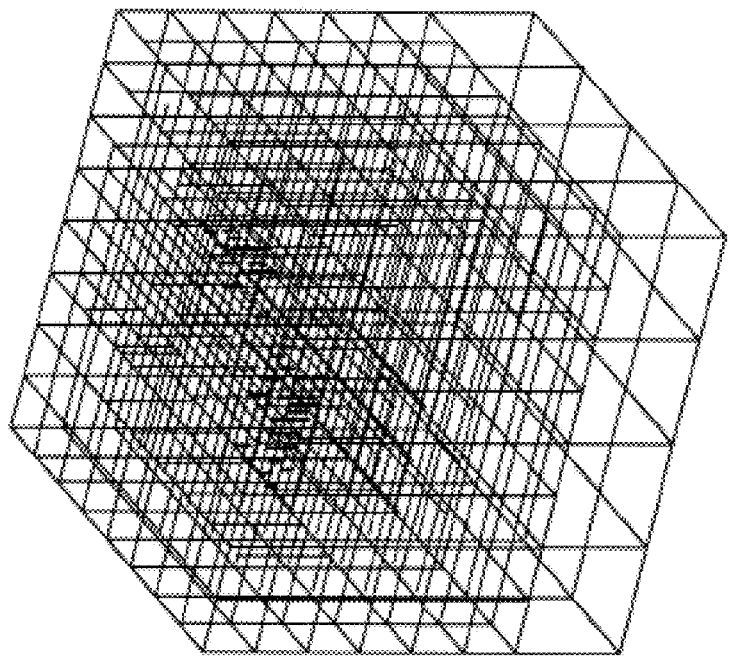
Figure 10B:
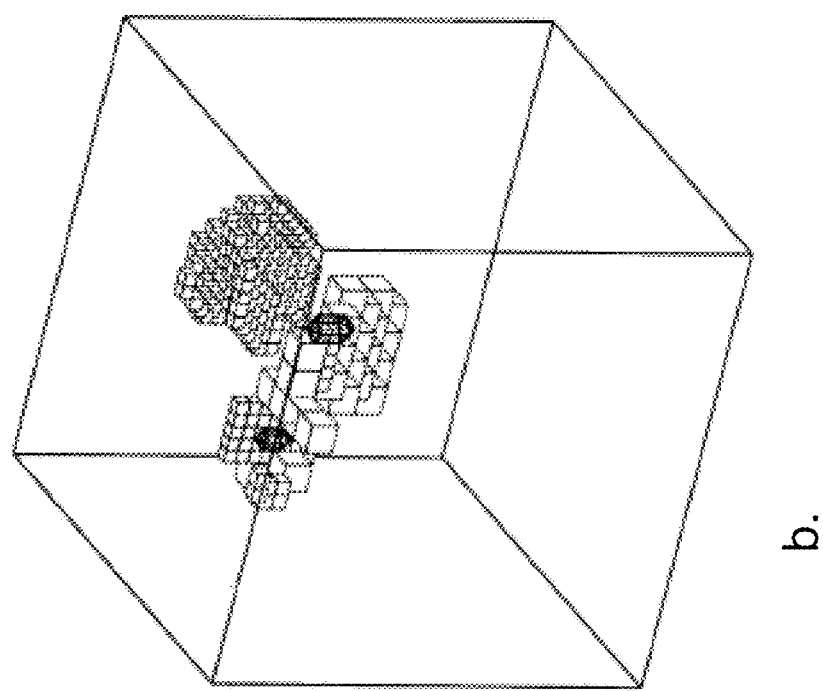
Figure 10B:
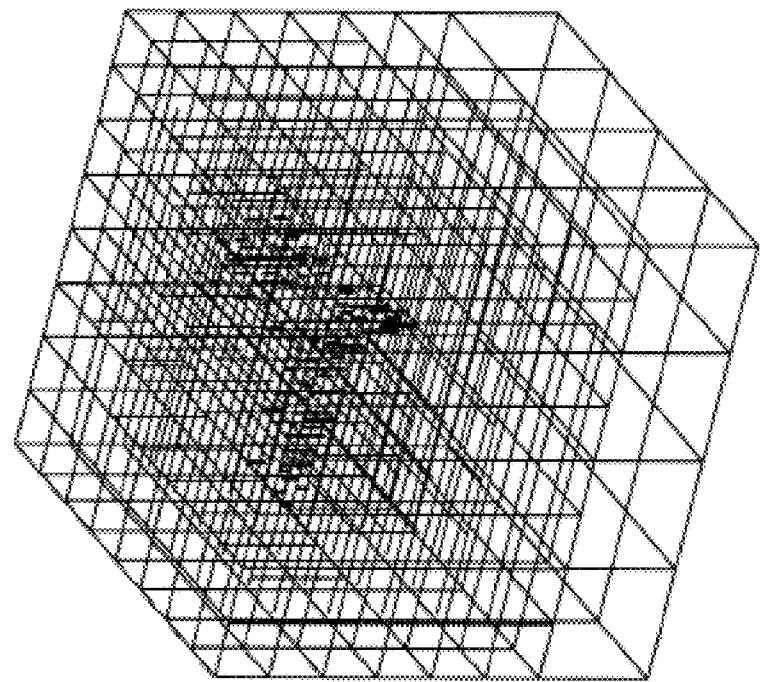
Figure 10C:
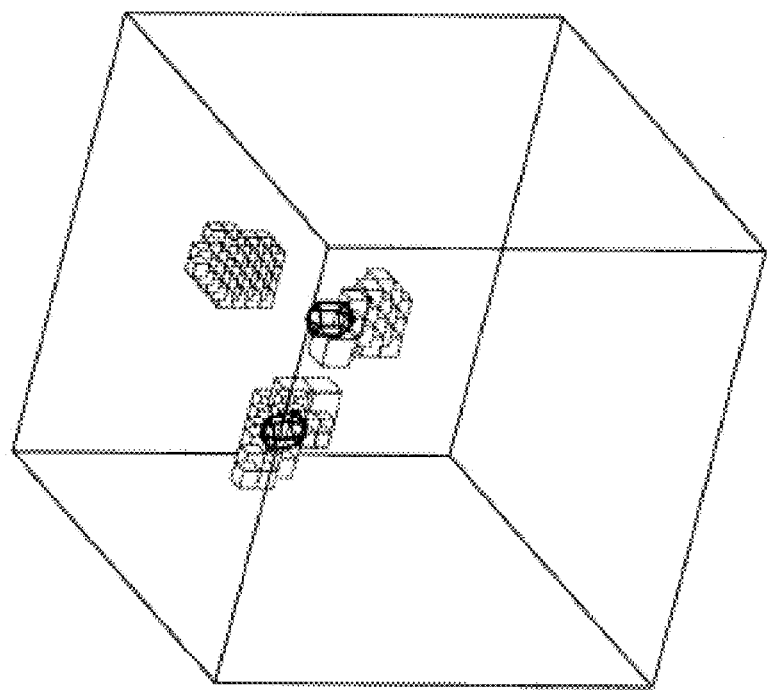
Figure 10C:
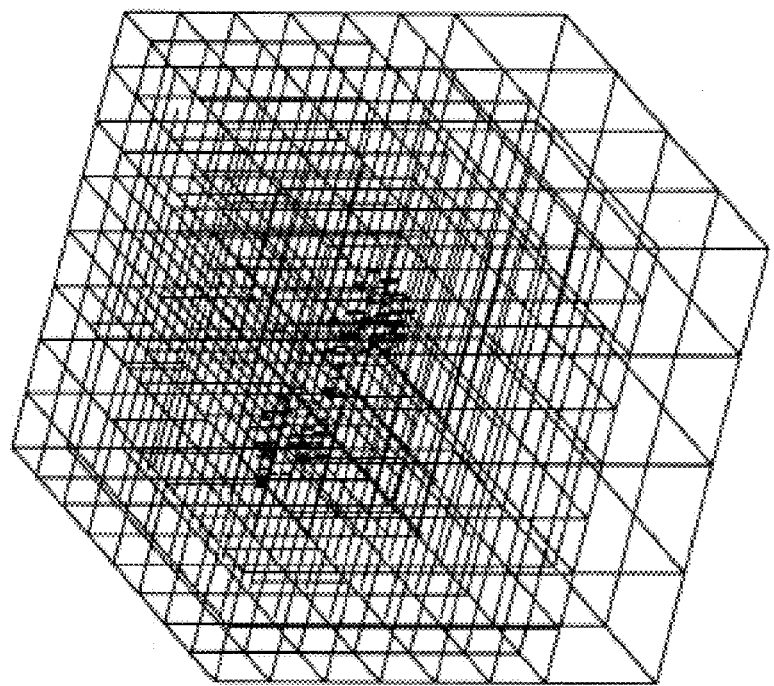

To access the difference in performance of the varied excitation source patterns, synthetic fluorescence measurements were generated for three targets placed at a depth of 1 cm from the illumination plane. FIG. 9 depicts the image reconstruction of three 1 cm deep fluorescent targets, performed with the synthetic data generated from (a) a single gaussian excitation source (half width=4 cm) centered on the illumination plane, (b) scanning line sources, (c) from four gaussian scanning excitation sources (half width=1 cm), and (d) the diffractive optics patterns. The advantage gained by multiple area illumination patterns is clear in this case, as the synthetic measurements generated by the single Gaussian source lack the information content to recover all three embedded fluorescent targets. In clinical situations, with multiple fluorescent targets, or a distributed fluorescence source in the tissue media, multiple area illumination will be a necessity for unambiguous image reconstruction. The additional computation burden introduced by employing multiple excitation illumination patterns is reduced by implementing the fluorescence tomography scheme in a parallel mode, wherein the forward and adjoint calculations for individual excitation sources are executed on separate threads, which can be easily distributed on to multiple processor computers. The performance of multiple source patterns can be further differentiated by placing the three fluorescent targets at different depths. The target depths used were 1 cm, 1.5 cm and 2.0 cm. FIGS. 10A-C depict the reconstructed images for different source patterns (a) to (c) The reconstructed parameter contour level cutoff needed to be reduced to 20% of the maximum level for resolving the three targets. The scanning gaussian sources (A) could not resolve the 1.5 cm deep and the 2 cm deep target clearly, while the scanning line source illumination (B) resulted in the detection of only the 1 cm and 1.5 cm deep targets. Diffractive optical pattern based illumination (C) provided the best image reconstructions as all the targets can be identified and there is no overlap at the 20% contour level cutoff.

EXAMPLE 2

Animal Model

Yorkshire swine were chosen as imaging subjects because the swine dermis and lymphatic network is considered to be similar to human. The animal was anesthetized, intubated, and maintained with isoflurane to prevent movement. A two month old 60 lb female swine was injected with 100 µL of Hyaluronan-I IRDye783 conjugate near the mammary chains. The fluorescence activity of the injected agent was equivalent to 32 µM indocyanine green solution. The dye injection was performed while imaging with a dynamic fluorescence imaging system which showed drainage of the injected contrast agent into the lymph nodes in swine groin. Hyaluronan binds with LYVE-1 receptor which is expressed only in lymphatic channels. After the excess agent was flushed away by the lymphatic pulsing, the vessels and the nodes were observed to be stained with the fluorescence agents and an almost steady state fluorescence signal was observed. Datasets for tomographic imaging were acquired 4 hours after the injection. The animal was euthanized after data acquisition and the lymph nodes were resected by a surgeon.

Imaging System

Figure 11:
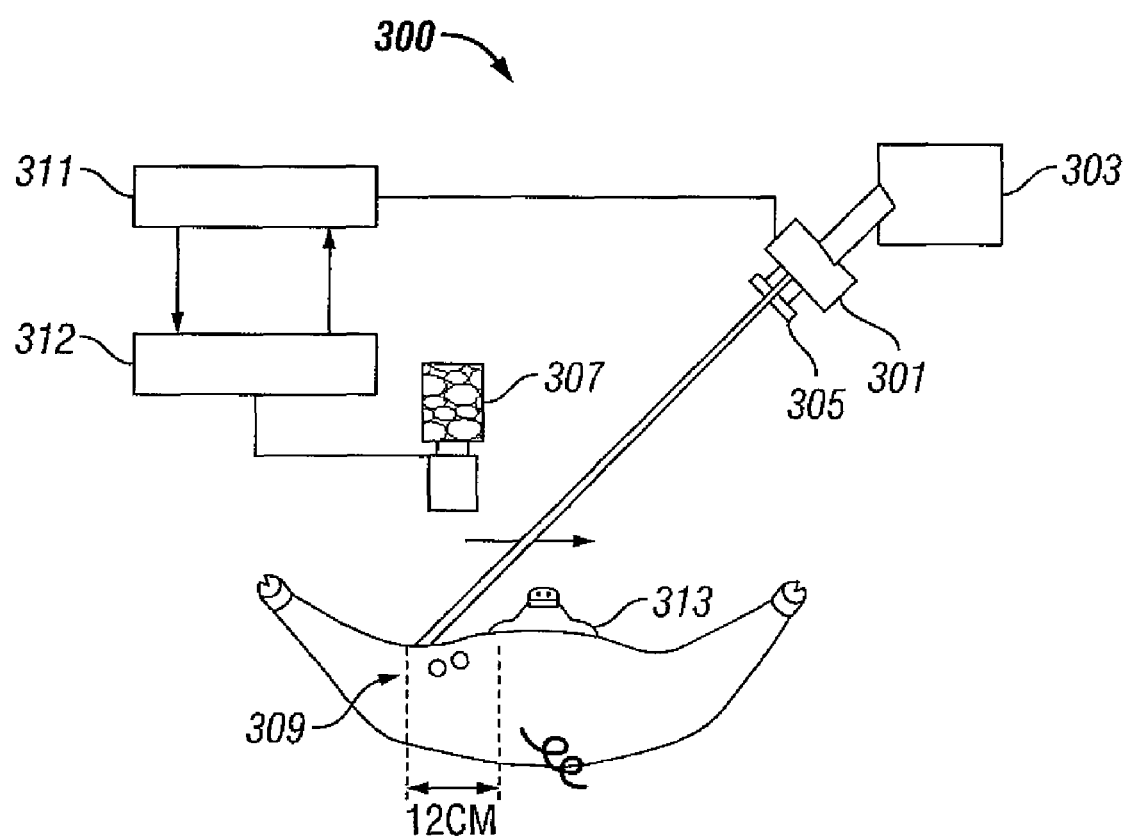
FIG. 11 illustrates an in vivo imaging system set-up.
Figure 12A:
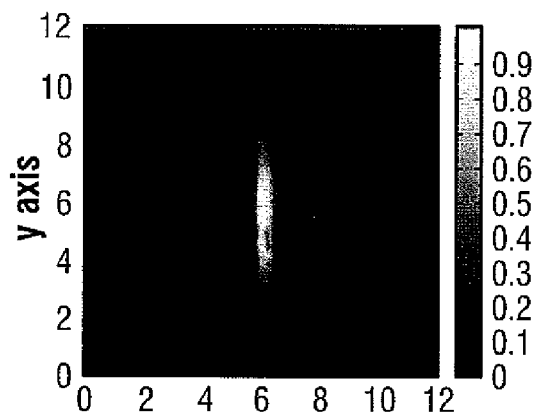
FIGS. 12(a)-(c) depict sample images acquired with the spatially patterned excitation based fluorescence imaging system: (a) steady state excitation image (arbitrary units (a.u.)), (b) emission amplitude (a.u.), (c) emission phase (radians)
Figure 12B:
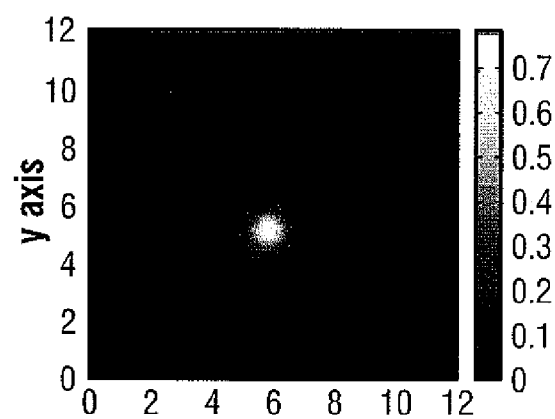
Figure 12C:
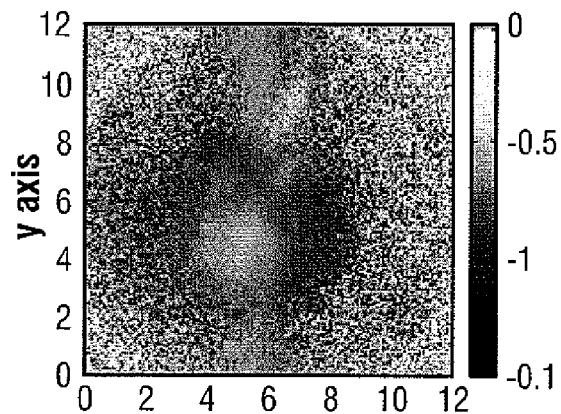

A modified homodyne gain modulated image intensifier based CCD camera setup 300 was used to acquire frequency domain fluorescence measurements. The major components of the system are illustrated in FIG. 11. A 785 nm laser diode 301 was mounted on a stepper motor 303 to enable scanning across the tissue surface 313 (i.e. Yorkshire swine) at the desired tissue 309 volume. The laser light was shaped into an approximately 4 mm wide line by using a cylindrical lens 305. Images were acquired by an intensified CCD camera 307. For each laser line position on the tissue surface, frequency domain data in the form of amplitude and phase distribution on the tissue surface was acquired for excitation (785 nm) and emission (830 nm) wavelengths. Frequency domain measurements were acquired in a homodyne mode by employing two phase locked oscillators 311 and 312. Oscillator 311 was used to modulate the gain of the laser diode at 100 MHz, while the oscillator 312 modulated the gain of image intensifier at 100 MHz. FIG. 12 depicts sample excitation and emission images acquired by the system 300.

Results

Figure 13A:
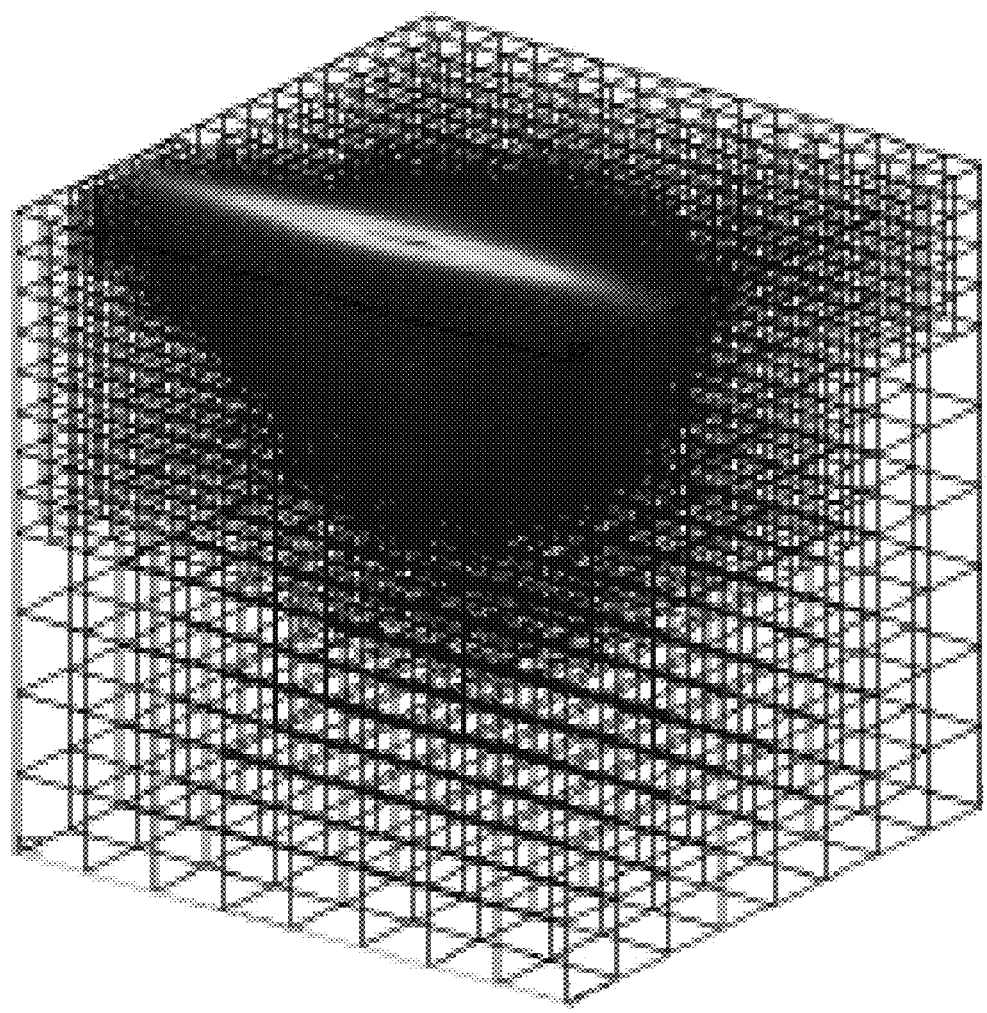
FIGS. 13A-C illustrate model based tomographic reconstructions from experimental fluorescence measurements on Swine lymph nodes: (A) adaptively refined forward mesh depicting the first source position, (B) final adaptively refined parameter reconstruction mesh, and (C) contour map and cutplanes drawn though the parameter reconstruction mesh depicting the reconstructed lymph node location.
Figure 13B:
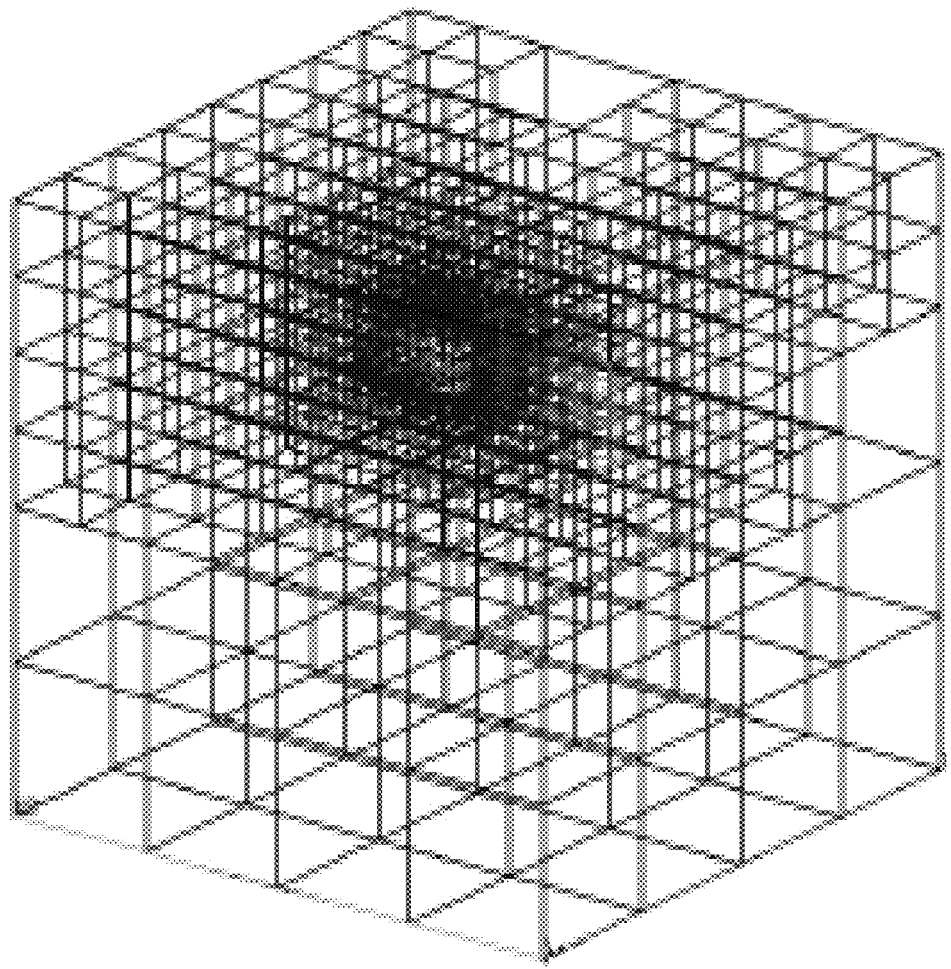
Figure 13C:
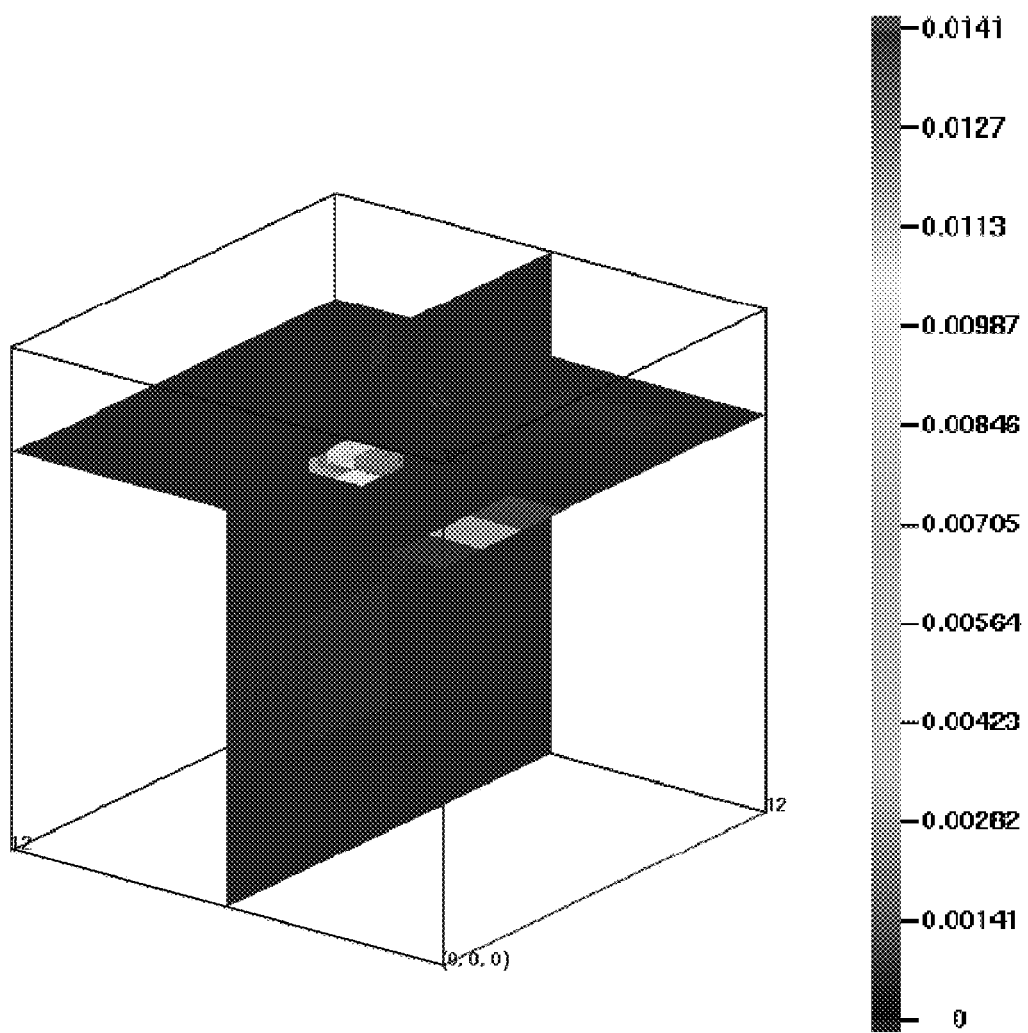

Measurements corresponding to 6 line sources positioned symmetrically about the suspected lymph node location (as ascertained from the 2-D images) were employed. A 12 cm cubical region around the suspected node location was used as the measurement and image reconstruction volume. For carrying out the finite element computation, hexahedral grids were used. Initial discretization level for all sources was kept at 1 cm, while for the unknown image the initial mesh resolution was 2 cm. As the Gauss-Newton parameter update iterations were processed, the meshes for forward/adjoint computations were refined to better resolve the laser line source positions and accurately solve the photon diffusion equations, while the parameter mesh were resolved to better delineate the target and coarsen the mesh in the regions away from the suspected target location. No further image update was obtained after 26 Gauss-Newton iterations during which 7 automatic mesh refinements/derefinements were triggered. FIG. 13 A depicts the final refined meshes for the first excitation line source. FIGS. 13 B-C depict the final parameter mesh and the slice plane drawn through the reconstructed $\mu_{axf}$ map. The depth of the reconstructed target was 2.5 cm which agreed with the observation of the surgeon that the resected lymph node in the imaged location was 2.5-3 cm deep.

While embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A method of imaging at least one fluorescent target in a medium, comprising:

a) illuminating a surface of the medium with light from at least one excitation light source to project at least two patterns on the surface, wherein each pattern comprises at least one motif;

b) for each pattern, measuring excitation light reflected from the medium to generate an excitation data set;

c) for each pattern, measuring fluorescence emitted from the at least one fluorescent target to generate a fluorescence data set;

d) generating a 3D image of the at least one fluorescent target by applying an iterative algorithm, wherein the iterative algorithm minimizes the difference between a predicted data set based on a mathematical model, and each excitation data set and each fluorescence data set.

2. The method of claim 1, wherein the motif has at least two edges.

3. The method of claim 1 wherein the motif is a polygon.

4. The method of claim 1 wherein the motif comprises a line, a ring, a cross, a star, concentric rings, a wavy line, a checkerboard, a spiral, or combinations thereof.

5. The method of claim 1, wherein the motif comprises a circle, an oval, a dot, or combinations thereof.

6. The method of claim 1 wherein at least one pattern comprises a plurality of motifs.

7. The method of claim 1 wherein at least one pattern is generated by diffractive optics.

8. The method of claim 1 wherein at least one pattern is generated by a beam shaper.

9. The method of claim 1 wherein a) comprises illuminating the surface of the medium to project at least two patterns sequentially.

10. The method of claim 1 wherein a) comprises illuminating the surface of the medium to project at least two patterns simultaneously.

11. The method of claim 1 wherein the excitation light source is a continuous wave light source.

12. The method of claim 1 wherein the excitation light source is a Gaussian light source.

13. The method of claim 1 wherein the intensity of the excitation light source is varied with time.

14. The method of claim 13 wherein the intensity of the excitation light source is varied by sinusoidal modulation, square wave modulation, or ramp wave modulation.

15. The method of claim 1 wherein the excitation light source is pulsed at a frequency or a repetition rate.

16. The method of claim 1 wherein the medium comprises living or biological tissue.

17. The method of claim 1 further comprising injecting the medium with a fluorescent contrast agent.

18. The method of claim 1 wherein the medium comprises a plurality of fluorescent targets.

19. The method of claim 18 wherein the plurality of fluorescent targets are at varying depths within the medium.

20. The method of claim 1 further comprising repeating steps a)-c) for different positions on the surface.

21. The method of claim 1 further comprising repeating steps a)-c) for more than two patterns.

22. The method of claim 1 wherein the iterative algorithm comprises an adaptive finite element method technique.

23. A system for imaging at least one fluorescent target in a medium, comprising: at least one excitation light source, excluding fiber optics, operable to illuminate a surface of the medium, wherein said excitation light source comprises a means for projecting at least two patterns on the medium, and wherein each pattern comprises at least one motif; a sensor that measures fluorescence emitted from the fluorescent target and excitation light reflected from the medium; and a computer that executes multiple fluorescence tomography calculations in parallel based on the measured fluorescence emitted from the fluorescent target and excitation light reflected from the medium.

24. The system of claim 23 wherein the motif has at least two edges.

25. The system of claim 23 wherein the motif is a polygon.

26. The system of claim 23 wherein the motif comprises a line, a ring, a cross, a star, concentric rings, a wavy line, a checkerboard, a spiral, or combinations thereof.

27. The system of claim 23 wherein the motif comprises a circle, an oval, a dot, or combinations thereof.

28. The system of claim 23 wherein the means for projecting at least two patterns on the medium is operable to illuminate the surface of the medium with the at least two patterns sequentially.

29. The system of claim 23 wherein the means for projecting at least two patterns on the medium is operable to illuminate the surface of the medium with the at least two patterns simultaneously.

30. The system of claim 23 wherein the means for projecting each pattern comprises a beam shaper.

31. The system of claim 23 wherein the means for projecting each pattern comprises diffractive optics.

32. The system of claim 23 wherein the excitation light source comprises a means for moving the pattern.

33. The system of claim 32 wherein the means for moving the pattern comprises a mirror, a prism, a motor, or combinations thereof.

34. The system of claim 23 wherein the sensor comprises an intensified charge-coupled camera.

35. The system of claim 23 wherein the computer comprises a parallel processing computer.

36. The system of claim 23 wherein the computer comprises a linux cluster.

37. The system of claim 23 wherein the at least one excitation light source is a time varying light source.

38. The system of claim 23 comprising a plurality of excitation light sources.

39. The system of claim 38 wherein the plurality of excitation light sources are operable to illuminate the surface of the medium with at least two patterns simultaneously.

40. The system of claim 38 wherein the plurality of excitation light sources are operable to illuminate the surface of the medium with at least two patterns sequentially.

* * * * *